(12) United States Patent
Kozlowski et al.

(10) Patent No.: US 8,676,604 B2
(45) Date of Patent: Mar. 18, 2014

(54) METHOD AND APPARATUS FOR MEDICATION PRESCRIPTION CONSULTATION

(75) Inventors: Casey L. Kozlowski, Barrington, IL (US); Gowri Selka, Buffalo Grove, IL (US); Natasha Polster, Long Grove, IL (US); Sam Libo, Deerfield, IL (US)

(73) Assignee: Walgreen Co., Deerfield, IL (US)

( * ) Notice: Subject to any disclaimer, the term of this patent is extended or adjusted under 35 U.S.C. 154(b) by 1522 days.

(21) Appl. No.: 11/839,306

(22) Filed: Aug. 15, 2007

(65) Prior Publication Data

US 2009/0048863 A1 Feb. 19, 2009

(51) Int. Cl.
*G06Q 10/00* (2012.01)
*G06Q 50/00* (2012.01)

(52) U.S. Cl.
USPC .................................................. 705/3; 705/2

(58) Field of Classification Search
USPC .............................................................. 705/3
See application file for complete search history.

(56) References Cited

U.S. PATENT DOCUMENTS

| | | | | |
|---|---|---|---|---|
| 5,845,255 A * | 12/1998 | Mayaud | | 705/3 |
| 6,014,631 A * | 1/2000 | Teagarden et al. | | 705/3 |
| 6,356,873 B1 * | 3/2002 | Teagarden et al. | | 705/3 |
| 6,578,003 B1 * | 6/2003 | Camarda et al. | | 705/3 |
| 6,694,298 B1 * | 2/2004 | Teagarden et al. | | 705/3 |
| 6,711,460 B1 * | 3/2004 | Reese | | 700/216 |
| 7,072,840 B1 * | 7/2006 | Mayaud | | 705/2 |
| 7,151,982 B2 * | 12/2006 | Liff et al. | | 700/241 |
| 7,483,839 B2 * | 1/2009 | Mayaud | | 705/2 |
| 7,519,540 B2 * | 4/2009 | Mayaud | | 705/2 |
| 7,574,370 B2 * | 8/2009 | Mayaud | | 705/3 |
| 7,630,788 B1 * | 12/2009 | Reese | | 700/216 |
| 8,589,186 B1 * | 11/2013 | Nadas et al. | | 705/3 |
| 2002/0032582 A1 * | 3/2002 | Feeney et al. | | 705/2 |
| 2002/0042725 A1 * | 4/2002 | Mayaud | | 705/2 |
| 2003/0144884 A1 * | 7/2003 | Mayaud | | 705/3 |
| 2005/0108053 A1 * | 5/2005 | Jones, Jr. | | 705/2 |
| 2007/0122783 A1 * | 5/2007 | Habashi | | 434/262 |

(Continued)

OTHER PUBLICATIONS

Johnson et al., Measuring the Impact of Patient Counseling in the Outpatient Pharmacy Setting: Development and Implementation of the Counseling Models for the Kaiser Permanente®/USC Patient Consultation Study, Clinical Therapeutics®, vol. 17, No. 5 (1995), pp. 988-1002.*

(Continued)

*Primary Examiner* — Michael Fuelling
(74) *Attorney, Agent, or Firm* — Francis C. Kowalik; Marshall, Gerstein & Borun LLP; Randall G. Rueth

(57) ABSTRACT

A method and apparatus of providing a pharmaceutical consultation prevents a person from receiving a medication prescription if consultation is required, and enables a user to readily view the medication prescription information and convey information to the person. Methods and apparatus of providing a pharmaceutical consultation are provided herein. The methods and apparatus include receiving medication prescription data relating to the medication prescription, and displaying a consultation review screen having a medication prescription view with information relating to the medication prescription and a discussion view with information to be conveyed to the person. The medication prescription data includes a consultation requirement for the medication prescription. A transaction for the medication prescription is prevented if consultation is required, and permitted when data is received indicating the consultation is completed. The methods and apparatus of pharmaceutical consultation also include remote consultation between a user and a person at different geographic locations.

34 Claims, 11 Drawing Sheets

(56) References Cited

U.S. PATENT DOCUMENTS

| | | | |
|---|---|---|---|
| 2008/0015893 A1 | 1/2008 | Miller et al. | 705/2 |
| 2008/0015894 A1 | 1/2008 | Miller et al. | 705/2 |
| 2009/0119129 A1* | 5/2009 | Nadas et al. | 705/3 |

OTHER PUBLICATIONS

Liptak, Adam, "Free Prozac in the Junk Mail Draws a Lawsuit," New York Times, Jul. 6, 2002, pp. A1 & A10.*

U.S. Appl. No. 11/458,059 entitled Optimization of a Medication Therapy Regimen, filed Jul. 17, 2006.

U.S. Appl. No. 11/458,054 entitled "Compliance With a Medication Therapy Regimen", filed Jul. 17, 2006.

U.S. Appl. No. 11/458,075 entitled "Appropriateness of a Medication Therapy Regimen", filed Jul. 17, 2006.

U.S. Appl. No. 11/458,080 entitled "Predictive Modeling and Risk Stratification of a Medication Therapy Regimen", filed Jul. 17, 2006.

* cited by examiner

METHOD AND APPARATUS FOR MEDICATION PRESCRIPTION CONSULTATION

TECHNICAL FIELD

The present disclosure relates generally to medication therapy management, and, more specifically, to pharmaceutical consultations.

BACKGROUND

Patients on a medication therapy regimen may take multiple medications, have multiple medical providers and/or have multiple medical conditions. In many cases, medication information, medical provider information and medical condition information are of particular medical importance in managing a patient's medication therapy regimen. For example, drug-drug interactions may occur in patients taking multiple prescription drugs and are the result of one or more drugs interacting with, or interfering with, another drug or set of drugs, thereby resulting in, for example, decreased efficacy, toxicity, etc. Drug-disease interactions result when a medication intended for treatment of one disease is in conflict with the treatment of a different disease in the same patient. Avoiding drug conflicts, such as drug-drug, drug-illness and drug-age interactions, increases the safety and efficacy of prescription drugs. Duplication of a drug or class of drugs may result in an overdose. In other cases, failure to adhere to a medication therapy regimen may adversely affect the patient's health.

In addition to medical importance, medication information and medical condition information are important from an efficiency perspective. For example, duplication of a medication may result in an increased cost without any additional medical benefit, as well as a potential medical disadvantage. In some cases, medications may be replaced or combined by prescribing an alternative medication that has an improved medical effect and/or may also result in decreased cost to the patient. Still further, many patients may not be well-versed or fully versed in the details regarding a medication prescription, including major or minor side effects, storage instructions, dosage/ingestion instructions, reasons for taking the medication, a description of the medication, etc. Accordingly, consultation with the patient about the medication prescription may be particularly useful, and in some cases may be of particular importance to the welfare of the patient.

In some cases, a consultation with the patient may be required, either by government or industry regulations, due to the importance of the consultation (e.g., identified adverse health risk, a potential replacement medication, etc.) or due to the professional opinion of the pharmacist. In such situations, the patient should not be permitted to fill or refill a medication prescription without first consulting with a pharmacist or other qualified pharmaceutical professional. In other situations, consultation may not be required, but may be requested by the patient.

However, patients often use different pharmacists, or pharmacies, to fill their prescriptions, such that data relating to the patient's medication prescription is provided by disparate data sources (e.g., different pharmacies). As a result, it may be difficult for any one pharmacist or other qualified professional to provide a comprehensive consultation to the patient. As a result, in many instances the patient and/or the patient's pharmacist is not fully apprised of the patient's medication prescription and associated information. Even if the information is available, it may be difficult for the pharmacist to remember or access all of the patient's information in order to provide a comprehensive consultation.

In other instances, a pharmacist may not be readily available to provide a consultation, which may result in denying the patient of needed medication due to a consultation requirement, even if only temporary. For example, a pharmacy's store hours or a pharmacist's hours may not coincide with the patient attempt to fill or refill a medication prescription. Alternatively, a pharmacist or other professional qualified to perform the consultation may not conveniently reside or be employed in the patient's geographic location. In such instances, a pharmacist at another location may be available to provide the consultation, but due to the patient's mobility and/or the distance between the geographic locations, consultation is impractical and the pharmacist may not have ready access to the patient's medication prescription information.

DETAILED DESCRIPTION

It should be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
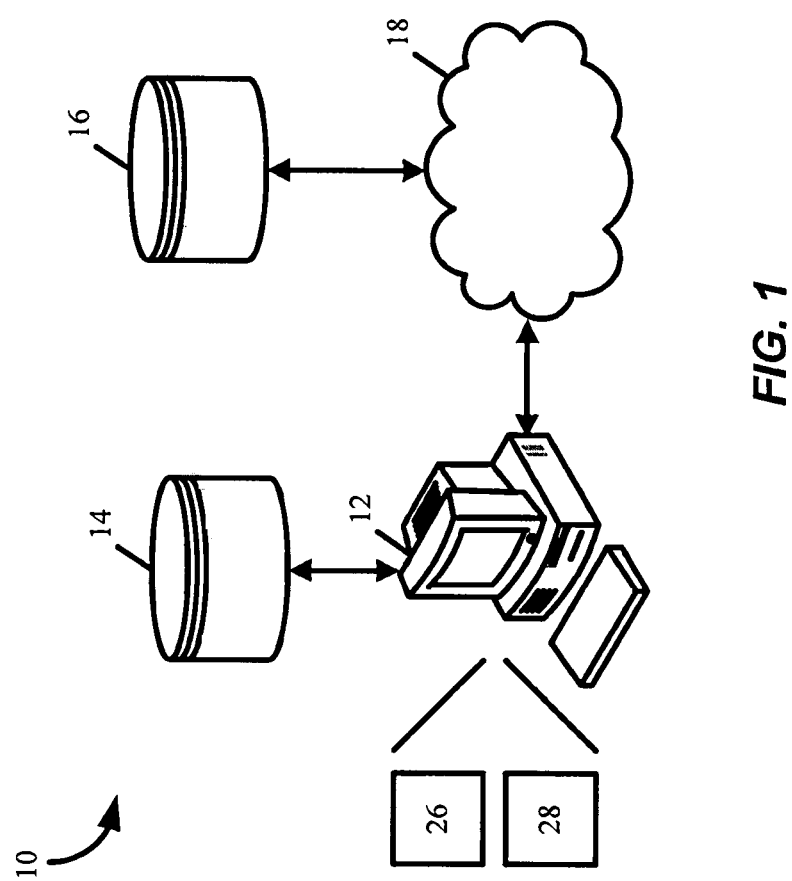
FIG. 1 is a block diagram of an embodiment of an intelligent network system for providing medication prescription consultations.

FIG. 1 is an exemplary schematic block diagram of an example of a data network and system 10 for providing medication prescription consultation. Referring to FIG. 1, the data network 10 may include a workstation 12 and a plurality of data sources 14, 16 communicatively coupled to the workstation 12. Although only one workstation 12 is depicted, it should be understood that the system 10 may include many workstations 12 at the same geographic location (e.g., the same pharmaceutical facility) and/or different geographic locations (e.g., different pharmaceutical facilities), an example of which is provided below. Likewise, although only two data sources 14, 16 are depicted, it should be understood that the system 10 may include many data sources 14, 16 communicatively coupled to the workstation 12 via a network 18.

In one example, one of the data sources 14 may be provided as a local data source, which may reside at the same geographic location as the workstation 12, and the other data source 16 may be provided at a different geographic location remote from the workstation 12 and remote from the local data source 14. The data source 16 may be a centralized data source for multiple workstations 12 and/or a local data source of another workstation which is accessible by other remote workstations 12. The workstation 12 may be a personal computer, a network terminal or the like provided at a pharmaceutical facility, such as a pharmaceutical care center or a pharmaceutical store. The data sources 14, 16 may include databases or other memory systems that store medication prescription data for each of a plurality of persons. The local data source 14 may be provided as an internal database of the workstation 12, including, but not limited to, a hard drive, a random access memory, a read-only memory or a removable storage device such as an optical disk, a magnetic disk, a flash memory card, an external hard drive, a zip drive, etc. Alternatively, the local data source 14 may be provided as an external database, such as a network server or external hard drive. The central data source 16 may be provided as standalone database, such as a hard drive, a random access memory, a read only memory or a removable storage device such as an optical disk, a magnetic disk, a flash memory card, an external hard drive, a zip drive, etc. The central data source 16 may be provided as a server or as computer, including another workstation 12.

Each of the workstation 12, the local data source 14, and the central data source 16 are inter-operatively coupled via a network 18, which may comprise, for example, the Internet, a wide area network (WAN), a local area network (LAN) or a mesh network. The network 18 may be provided using a wide variety of techniques well known to those skilled in the art for the transfer of electronic data. For example, the network 18 may comprise dedicated access lines, plain, ordinary telephone lines, satellite links, combinations of these, etc. Additionally, the network 18 may include a plurality of network computers or server computers (not shown), each of which may be operatively interconnected in a known manner. Where the network 18 comprises the Internet, data communication may take place over the network 18 via an Internet communication protocol.

Although the data network 10 is shown to include one workstation 12, one local data source 14, and one central, data source 16, it should be understood that different numbers of workstations, local data sources and central data sources may be utilized. For example, the data network 10 may include a plurality of workstations 12, local data sources 14, and central data sources 16, all of which may be interconnected via the network 18. According to the disclosed example, this configuration may provide several advantages, such as, for example, enabling near real time uploads and downloads of information, as well as periodic uploads and downloads of information, if desired.

The local data source 14 may store medication prescription data for persons, such as patients and prescription consumers, that fill their prescriptions at the pharmaceutical facility where the workstation 12 is located. In order to efficiently utilize the amount of storage space, the local data source 14 may retain data for a specific time period, such as all medication prescriptions active within the past week to be filled or refilled, whereas data older than the specified time period is transferred to the central data source 16. The central data source 16 may store medication prescription data for all persons, such as all patients or prescription consumers, that fill their prescriptions at multiple pharmaceutical facilities, which may be affiliated with one another (e.g., a chain of pharmaceutical stores, members of a trade organization, members of a strategic partnership, etc.). The central data source 16 may also store medication prescription data from pharmaceutical care centers, pharmaceutical stores, employer and/or healthcare insurers, and medical providers, such as home care providers, hospitals, clinics and doctors.

Medication prescription data may include, but is not limited to, data related to identification of the person, data related to a medication being prescribed to the person, and data related to consultation information to be conveyed to the person. The identification data of the person may include details such as the person's name, address, phone number, birth date, social security number, insurance company provider, insurance policy identification, or any other information pertaining to the person. The medication data may include details about the medication being prescribed to the person, such as prescription number, medication name, medication description, prescribing doctor, prescription fill/refill dates, patient name, storage instructions, usage instructions or any other details regarding the medication. Although discussed in greater detail below, consultation information may include usage instructions for taking the medication in addition to those provided with the medication data, medication purpose, actual or potential side effects, emergency instructions, and further information and/or instructions as may be associated with the medication. Consultation information may further include personal comments, remarks or observations by a pharmaceutical professional, such as a pharmacist, and consultation instructions for the pharmaceutical professional providing the consultation. Still further, the consultation information may include message or alert information, such as an identified adverse health outcome associated with utilization of the medication, a replacement medication, availability of a generic medication, or fill/refill alerts. Of course, it should be understood that the particulars about the consultation information are not limited to the examples provided, but may relate to additional information that may be useful in consulting a person about a medication prescription.

It should further be understood that each of the workstations 12, local data sources 14, and central data sources 16 may be coupled to the data network 10 by a network computer which may include a processor, a memory operatively coupled to the processor and/or a database operatively coupled to the processor and memory. In some instances, each workstation 12, local data source 14, and central data source 16 may maintain its own internal data network, such that the workstation 12 may be one of a plurality of workstations at a pharmaceutical facility, the local data source 14 may be one of a plurality of databases or servers such as an array databases or servers, and the central data source 16 may be one of a plurality of databases or servers such as an array of databases or servers. The network computer may be a server computer of the type commonly employed in networking solutions.

Figure 2:
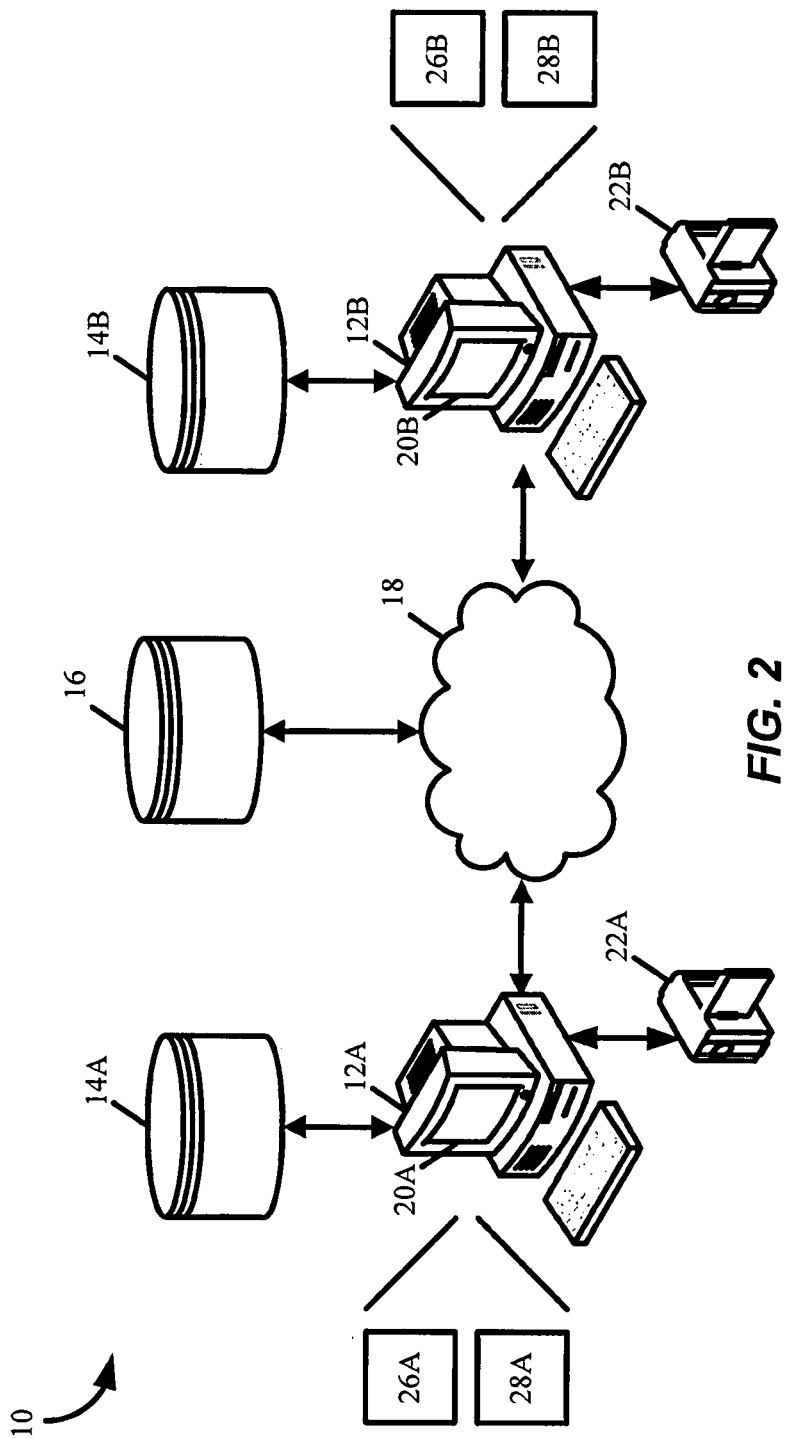
FIG. 2 is a block diagram of an embodiment of an expanded intelligent network system of FIG. 1 for providing remote medication prescription consultations.

FIG. 2 is an exemplary schematic block diagram of an expanded view of the data network 10 for providing medication prescription consultation between a workstation 12A at a first geographic location and a workstation 12B at a second geographic location remote from the first geographic location. Each of the workstations 12A, 12B may be coupled to a respective local data source 14A, 14B and to one or more central data sources 16 via a network 18. Each of the workstations 12A, 12B, local data sources 14A, 14B and central data source 16 may correspond to the workstation 12, local data source 14 and central data source 16 described above with reference to FIG. 1.

Each of the workstations 12A, 12B may include a display 20A, 20B and a communication device 22A, 22B for real-time correspondence between a person, such as a patient or pharmaceutical consumer, at the workstation 12A and a user, such as a pharmaceutical professional or other person that provides the pharmaceutical consultation, at the workstation 12B. Real-time correspondence between a person and the user thereby facilitates real-time consultation between remote locations. In one example, each of the communication devices 22A, 22B may include a video communication device, such as a video camera, microphone and speaker, to facilitate real-time remote video conferencing between the workstations 12A, 12B. The video communication device 22A at the first geographic location may thereby convey a real-time image of a person from the first geographic location to the workstation 12B at the second geographic location which may be displayed on the display 22B. Likewise, the video communication device 22B at the second geographic location may convey a real-time image of the user from the second geographic location to the workstation 12A at the first geographic location which may be displayed on the display 22A.

Although real-time correspondence is beneficial for consultation between a person and a user located at different geographic locations, it should be understood that real-time correspondence refers to actual real-time correspondence or near real-time correspondence, with the understanding that minor transmission delays may occur between the time a communication (e.g., data packet) is sent from a transmitting workstation and the time it is received at the receiving workstation. As such, quality of service considerations may be accounted for in determining the communication devices 22A, 22B to be employed in order to provide real-time correspondence. It should further be understood that communication devices 22A, 22B may be provided as an alternative to, or in addition to, video communication devices. For example, additional communication devices 22A, 22B may include communication devices for an instant messaging system, such as a modem, associated software and communication protocols, to facilitate instant messaging between the workstations 12A, 12B. Communication devices 22A, 22B may also be provided as solely audio communication devices, such as a microphone and speaker. A further example of real-time communication between, workstations 12A, 12B is provided below. In each of the communications between and among the workstations 12, the local data sources 14 and the central data sources 16, the communication may be encrypted, transmitted via a secure network protocol or otherwise secured against unauthorized access and interception.

Each workstation 12 may include a consultation application 26 stored on a memory of the workstation 12 (shown in FIG. 2 as 26A and 26B for each respective workstation 12A, 12B), or each workstation 12 may otherwise access the consultation application 26 stored on another memory device or other computer readable medium. The consultation application 26 provides a workflow process for users to consult persons regarding a medication prescription and record the outcome of the consultation. The consultation application 26 allows consultation to be performed at any location with a workstation 12, including consultation between two geographically remote locations, an example of which is shown in FIG. 2 and described further below. As such, the consultation application 26 facilitates consultations "on-site" at a pharmaceutical facility.

The consultation application 26 facilitates a consultation between the user and the person after a medication prescription has been prepared for the person, for example after the medication prescription has been printed for the person at the pharmaceutical facility when the person is in the process of filling the prescription. In particular, once a medication prescription is entered into the local data source 14 and/or the central data source 16, various criteria of the medication prescription may be checked using a rules engine 28, which may reside on each workstation 12 (shown in FIG. 2 as 28A and 28B for each respective workstation 12A and 12B). Alternatively, the rules engine 28 may be provided centrally (e.g., with the central data source 16), and accessed by the workstation 12 or the consultation application 26. However, it is noted that the workstation 12 or the consultation application 26 may be limited to accessing only results provided by the rules engine 28 as opposed to the actual functions of the rules engine 28. Some of the criteria that the rules engine 28 may take into account include an assessment of the person's health risk, a assessment of the person's compliance with a medication or medication regimen, an identification of inappropriate medications being taken by the person, optimization of a person's medication regimen, predictive modeling and risk stratification, and an assessment of the appropriateness of the person's medication regimen. For example, adverse health outcomes or medication interchanges that have been identified by a rules engine 28, may cause a medication prescription to be flagged for a mandatory consultation. Examples for evaluating and executing the various criteria are described in U.S. Patent Application Publication No. 2008/0126117 entitled "Optimization Of A Medication Therapy Regimen" filed on Jul. 17, 2006, U.S. Patent Application Publication No. 2008/0015893 entitled "Identification Of Inappropriate Medications In A Medication Therapy Regimen" filed on Jul. 17, 2006, U.S. Patent Application Publication No. 2008/0126130 entitled "Compliance With A Medication Therapy Regimen" filed on Jul. 17, 2006, U.S. Patent Application Publication No. 2008/0097784 entitled "Appropriateness Of A Medication Therapy Regimen" filed on Jul. 17, 2006, U.S. Patent Application Publication No. 2008/0126131 entitled "Predictive Modeling And Risk Stratification Of A Medication Therapy Regimen" filed on Jul. 17, 2006, and U.S. Patent Application Publication No. 2008/0015894 entitled "Health Risk Assessment Of Medication Therapy Regimen" filed on Jul. 17, 2006, each of which are incorporated by reference herein in their entirety for all purposes.

Additional criteria for requiring consultation may include regulatory requirements. For example, some regulatory requirements require a pharmacist providing the medication to consult the person for all new medication prescriptions, for all refills on a medication prescription and for persons of a certain age (e.g., minors). As such, medication prescription data pertaining to a new medication prescription may include an indicator that consultation is required. In particular, when a new medication prescription is entered into one of the data sources 14, 16, an entry is provided in the medication prescription data to indicate the consultation requirements associated with the medication prescription, and particularly in the consultation data (e.g., consultation, history) of the medication prescription data. An indicator that consultation is mandatory is set in the medication prescription data based on various rules for consultation, including those described above and below.

If the rules engine 28 determines the medication prescription requires consultation, the medication prescription data associated with the medication prescription is marked or appended with data indicating that a consultation requirement is associated with the medication prescription. As such, the medication data for each prescription stored, in the data sources 14, 16 may include indication data indicating a consultation requirement associated with the medication prescription. When the indication data indicates that consultation is mandatory, a transaction involving the medication prescription (e.g., sale of the medication to the person) may be prevented at the time of, or prior to, the transaction (e.g., point-of-sale). The user is alerted that a consultation is required and utilizes the consultation application 26 to facilitate the consultation. Once the consultation has been performed, with an indication that consultation is completed provided to the consultation application 26, may the medication prescription data be updated to reflect as much and the transaction be allowed to complete for a medication prescription with mandatory consultation. The user is able to add comments regarding the consultation, and the comments may also be stored as part of the medication prescription data.

Figure 3:
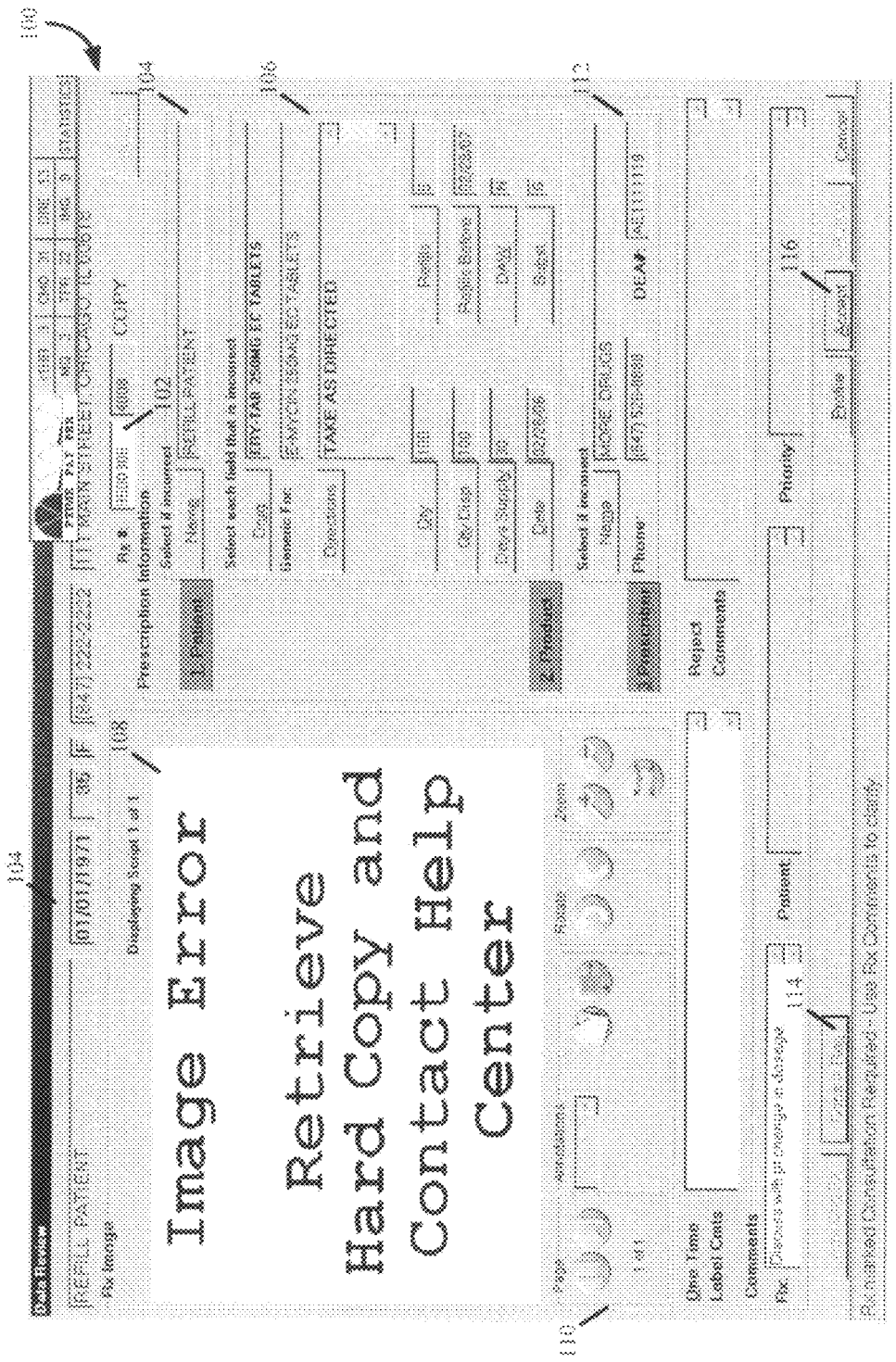
FIG. 3 is an exemplary graphical display that may be provided by a graphical user interface to enable a user to provide an indication that a consultation for a medication prescription is mandatory.

Although consultation may be determined by a rules engine 28, consultation may also be requested by the user or another pharmaceutical professional. FIG. 3 is an exemplary graphical display of a medication prescription data review screen 100 that may be provided by a graphical, user interface to enable a user to provide an indication that a consultation for a medication prescription is mandatory. The graphical display 100 provides the user with information pertaining to a medication prescription in the local data source 14 and/or the central data source 16, and allows the user to access and modify various aspects of the medication prescription.

As can be seen, the medication prescription data review screen 100 provides a prescription identifier view 102 which displays an identification of the medication prescription being reviewed, such as a prescription number, along with information about the person associated with the medication prescription in a patient information view 104. In particular, a user may identify the medication prescription to be reviewed, for example by entering the prescription identification number in the prescription identifier view 102 or by scanning a barcode of the medication prescription, in order to generate the medication prescription data in the medication prescription data review screen 100. In response thereto, the patient information view 104 may display information such, as the name, date of birth, age, gender, contact information of the person and the like. Details about the medication prescription are provided in a medication information view 106, including, but not limited to, the name of the medication, directions, supply/quantity information and prescription fill/refill information.

In addition to details about the medication prescription as shown in the medication prescription view 106, the medication prescription review screen 100 may also include an image 108 of the medication associated with the medication prescription or an image of the physical medication prescription as originally prescribed by a medical professional, such as the person's doctor. An image 108 of the medication and/or the original medication prescription may be used by the user to verify the information provided in the medication, prescription view 106, and vice versa, to avoid mistakes in filling the medication prescription. The user may be provided with image controls, shown here as graphical representations 110, to manipulate the image as needed.

Details about the person prescribing the medication, such as a doctor or other medical professional, are provided in a prescriber information view 112, including the prescriber's name, contact information and professional identification. As a result, a user may contact the prescriber directly if any questions arise regarding the medication prescription during the review of the medication prescription data. The medication prescription data review screen 100 may further enable the user to modify any of the information provided in any of the views 102, or may restrict the user from modifying any of the information.

The user may also be enabled to accept the information provided in each of the views 104, 106, 112, as well as provide his/her own comments regarding the review of the medication prescription. Notably, the medication prescription data review screen 100 enables the user to require consultation before the person can fill the prescription, shown here as a graphical representation of a "Consult Req" button 114. That is, the user may request that consultation is mandatory using his/her own professional judgment and knowledge, as opposed to a rules engine 28 that determines a potential adverse health risk, for example. The user is thereby provided with the flexibility to consult with the patient for any reason, such as emphasizing the importance of adhering to the medication regimen, adhering to the directions for taking the medication, adhering to the fill/refill schedule for the medication, etc. In response to requesting or otherwise establishing a mandatory consultation, for example by selecting the "Consult Req" button 114 using a mouse or keyboard, the medication prescription data for the medication prescription may be flagged or otherwise associated with an indication that consultation is required, and the person may be prevented from completing a transaction for the medication prescription until consultation has been completed. However, the user may be prevented from requiring consultation until all other information about the medication prescription has been accepted by the user, as indicated by selecting a graphical representation of an "Accept" button 116. Once the user has selected the "Accept" button 116, the "Consult Req" button 114 may be activated such that it may be selected by the user.

It is noted that even medication prescriptions having indication data indicating that a consultation is not required may nonetheless involve consultation using the consultation application 26, just not as a prerequisite for completing the transaction for the medication prescription. In other words, the consultation application 26 may be utilized for medication prescriptions where consultation is optional. If the medication prescription data indicates the consultation is optional (i.e., not required), the person may either consent to the consultation or refuse the consultation, with the consent or refusal being stored as additional medication prescription data and the transaction being allowed to complete in either the case of acceptance or refusal. The consultation application 26 also allows for the user to add comments regarding the consultation, once the optional consultation is completed, and the comments may be stored as part of the medication prescription data.

One important aspect of the systems of FIGS. 1 and 2 is a user interface routine associated with the consultation application 26 and which provides a graphical user interface (GUI) that is integrated with the consultation application 26 described herein to facilitate a user's interaction and consultation with the person. FIGS. 4-11 provide exemplary displays of the GUI that may be generated by the consultation application 26 in order to facilitate consultation between the user and the person. However, before discussing the GUI in greater detail, it should be recognized that the GUI may include one or more software routines that are implemented using any suitable programming languages and techniques. Further, the software routines making up the GUI may be stored and processed within a single processing station or unit, such as, for example, a workstation 12 within a pharmaceutical facility or, alternatively, the software routines of the GUI may be stored and executed in a distributed manner using a plurality of processing units that are communicatively coupled to each other within the system 10.

Preferably, but not necessarily, the GUI may be implemented using a familiar graphical windows-based structure and appearance, in which a plurality of interlinked graphical views or pages include one or more pull-down menus, buttons or other graphical representations that enable a user to navigate through the pages in a desired manner to view and/or retrieve particular types of information regarding the medication prescription. The features and/or capabilities of the consultation application may be represented, accessed, invoked, etc. through one or more corresponding pages, views or displays of the GUI. Furthermore, the various displays making up the GUI may be interlinked in a logical manner to facilitate a user's quick and intuitive navigation through the displays to retrieve a particular type of information or to access and/or invoke a particular capability of the consultation application.

Generally speaking, the GUI described herein provides intuitive graphical depictions or displays to search and provide information relating to the medication prescription of the person. Each of these graphical displays may include particular medication prescription information that is associated with a particular view being displayed by the GUI. For example, a display for searching for a person's medication may be provided, with medication prescriptions resulting from the search displayed for the user to select in order to display further information about the selected medication prescription. On the other hand, a display depicting a consultation review may provide information to be conveyed to the person regarding the medication prescription, in addition to information to aid the user in providing the consultation. In any event, a user may use the information shown within any view, page or display to quickly access information about the medication, prescription and convey appropriate information to the person.

Additionally, the GUI described herein may automatically, or may in response to a request by a user, provide a display depicting a consultation history having a table of information relevant to previous consultations with the person. The consultation history information may be provided by a local data source 14 or a central data source 16. Similarly, the GUI may display alerts and messages regarding a replacement medication or availability of a generic medication. Still further, the GUI may display alerts and messages relating to medication utilization to the user in connection with a problem that has been identified as potentially causing an adverse health outcome. These messages may include graphical and/or textual information that describes the problem, suggests possible solutions which may be implemented to alleviate an identified problem or which may be implemented to avoid a potential problem, describes courses of action that may be pursued to correct or to avoid a problem, etc.

The consultation application 26 may therefore include the graphical user interface and the features described herein. Generally, the consultation application GUI may be presented as a series of windows or display screens having one or more views each for various types of information. Each time a user logs into the consultation application 26 or uses the consultation application 26 to conduct a consultation, the user begins a new session of the consultation application 26. In addition, each window or display screen may include the initials or other identifying indicia of the user logged in to the consultation application session and a graphical representation of an option to logout of the consultation application session.

FIGS. 4-11 are exemplary graphical displays that may be provided by the GUI to enable a user at a workstation 12, such as a pharmacist or another qualified pharmaceutical professional, to provide a medication prescription consultation to a person and store results thereof as medication prescription data in the local data source 14 and/or the central data source 16. In particular, the graphical displays of FIGS. 4-11 may be utilized with respect to the consultation application 26, though it should be readily understood that similar graphical displays may be used with respect to consultations associated with the other medication prescription routines, including those disclosed in U.S. patent application Ser. Nos. 11/458,059, 11/458,066, 11/458,054, 11/458,075, 11/458,080, and 11/458,071, as referenced above.

Figure 4:
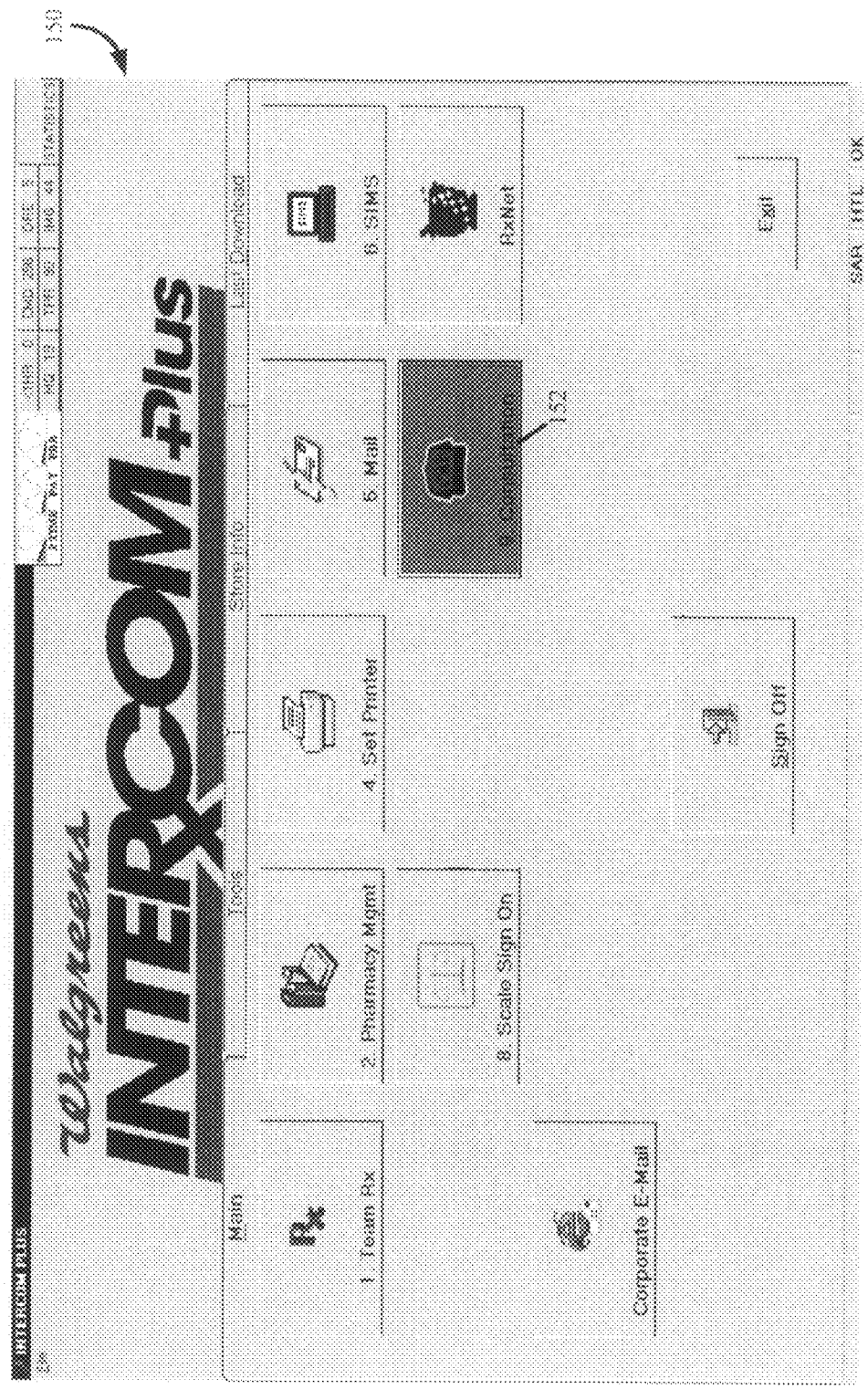
FIG. 4 is an exemplary depiction of a display that may be provided by a graphical user interface to initiate a consultation application to facilitate consultation regarding a medication prescription between a user of the consultation application and a person.

FIG. 4 illustrates an example screen display 150 that may be presented to a user to initiate the consultation application 26 in order to facilitate consultation regarding a medication prescription between a user of the consultation application 26 and a person. In particular, the display 150 includes several graphical representations, each of which may represent a different application within a suite of applications that may be provided to the user, including the consultation application 26. The graphical representation 152 of the consultation application 26 enables the user to initiate execution of the consultation application 26 by selecting the consultation application 26 using, for example, a keyboard, mouse, voice-response device, etc. Although several examples of graphical representations, such as buttons, data entries, etc., that may be selected by the user are described herein, it should be understood that each such graphical representation may be selected in a variety of manners using, for example, a keyboard, mouse, voice-response device, and the like, and need not be repeated in each instance that a graphical representation is described.

In one example, during a transaction involving the medication prescription (e.g., during a fill or refill of the medication prescription), the prescription is printed with the medication. The printed prescription may include a printed indication that a consultation is mandatory, and may further include a summary of the reason for the consultation (e.g., a replacement medication available, medication utilization alert, consultation requested by a pharmaceutical professional, etc.). The printed prescription may also include an indication that a consultation is optional. The indication may be provided as an alphanumeric indication or a symbolic indication that a pharmaceutical facility personnel (e.g., pharmaceutical technician, pharmacist, etc.) will recognize as a mandatory or optional consultation. The pharmaceutical facility personnel may then advise the person that consultation is mandatory or optionally available. In the case of mandatory consultation, the pharmaceutical facility personnel prevents the transaction from being completed until consultation is completed, and alerts a user that the consultation is required, where the user is someone who is authorized to provide the consultation and utilize the consultation application 26.

In the case of optional consultation, the pharmaceutical facility personnel alerts a user who is authorized to provide the consultation and utilize the consultation application 26 that the consultation is requested by the person. Otherwise, the pharmaceutical facility personnel completes the transaction if the optional consultation is refused by the person, and the refusal is stored with the medication prescription, data via a computer or terminal used for the transaction (e.g., a checkout register, workstation 12, etc.).

In another example, the indication may be recognized by a transaction device, such as a barcode reader or computer, such that when a barcode printed on the prescription is scanned or a medication prescription identification number is otherwise entered, the pharmaceutical facility personnel is alerted to the consultation requirement (mandatory or optional) and any associated reasons for the consultation (replacement, alert, request, etc.). The alert may depend on whether the consultation is optional or mandatory and/or the reasons for the consultation. For instance, the pharmaceutical facility personnel may be presented with one of the following prompts: "Consultation Action—Accept/Refuse", "Interchange Prescription—Pharmacist Must Counsel", "Utilization Review—Pharmacist Must Counsel", "Pharmacist Request—Pharmacist Must Counsel". The first prompt is for an optional consultation prompting the pharmaceutical facility personnel to indicate whether consultation is accepted or refused, the second prompt is a medication interchange alert requiring consultation, the third prompt is a medication utilization alert requiring consultation and the fourth is a requested mandatory consultation. Of course, the above prompts are examples only, and the particulars of the prompts may be provided in a variety of manners such that they are understood by the person viewing the prompt.

The transaction device or the pharmaceutical facility personnel may then prevent completion of the transaction (e.g., refusal to accept monetary funds, prevention of credit card authorization, etc.) until consultation is completed as indicated in the medication prescription data or refused (if optional) as indicated in the medication prescription data in response to an input by the pharmaceutical facility personnel (e.g., accept/refuse). In the case the person refuses mandatory consultation, the refusal is indicated in the medication prescription data and the transaction is prevented. In the case the person accepts optional consultation, the acceptance is noted in the medication prescription data via the consultation application 26. If the person refuses optional consultation, the refusal may be noted in the medication prescription data without the use of the consultation application 26 and the transaction may be completed.

The pharmaceutical facility personnel may then notify the person that consultation is optional or mandatory. If consultation is accepted by the person, a user authorized to provide the consultation is alerted, at which point the user may meet with the patient at the workstation 12. The screen display 150 may be presented to the user via a display at the workstation 12 as an introductory display screen to enable the user to select the consultation application 26 upon being alerted that a consultation is requested or required.

Figure 5:
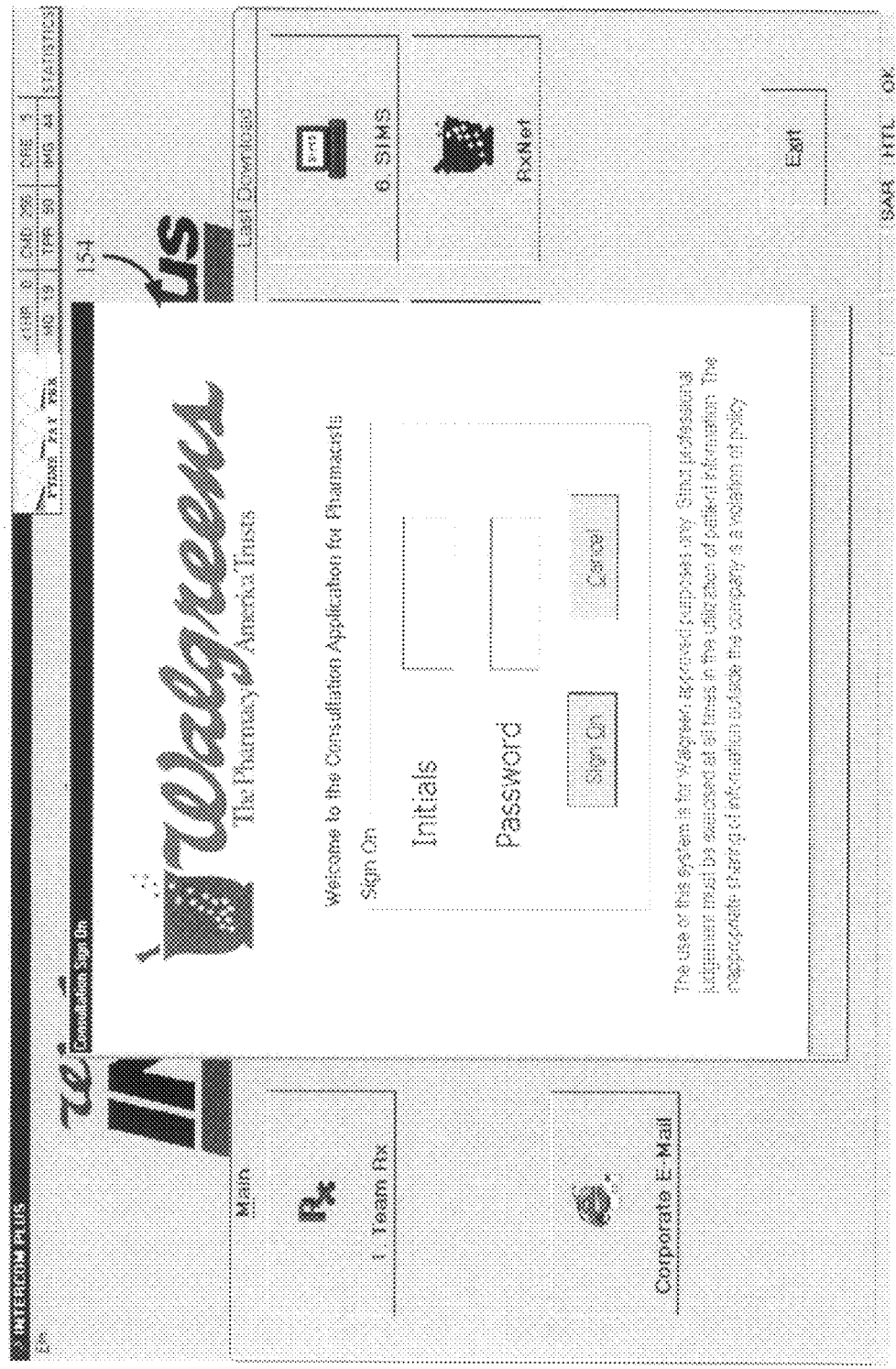
FIG. 5 is an exemplary graphical display that may be provided by a graphical user interface to verify the authenticity of the user using the consultation application.

FIG. 5 illustrates an example screen display 154 that may be presented by the consultation application 26 to a user in response to the user selecting the graphical representation 152 of the consultation application 26 from the display 150. In particular, the screen display 154 is provided by the graphical user interface to verify the authenticity of the user using the consultation application 26. The user may enter a user identification, such as the user's name, employee number, etc., and further enter a password uniquely associated with the user's identification. The password may be assigned to the user or chosen by the user, and may be periodically changed for security purposes. The user may then submit the entered username and password to be verified by the consultation application 26, or via a separate verification process which may reside locally, for example on the workstation 12, or remotely, for example on a centralized server within the system 10. If the information submitted by the user is not verified, for example if the provided password is not associated with the provided username, the user will not be granted access to the consultation application 26. Although a username and password combination has been described, it should be understood that a number of authentication processes may be utilized to verify the authenticity of the user and authorize the user to utilize the consultation application.

If the information submitted by the user is verified, the user is granted access to the consultation application 26, or at least as much as may be provided depending on the level of authorization, and hence level of access or utilization, that may be granted to the user. For example, pharmacists may be allowed full access to the consultation application 26, whereas pharmacy interns may be granted only limited access and pharmacy technicians may be denied all access. Once granted access to the consultation application 26, the user begins a session in the consultation application 26 for the person and may be presented with a consultation queue in order to retrieve medication prescription data for the person from the local data source 14 and/or the central data source 16.

Figure 6:
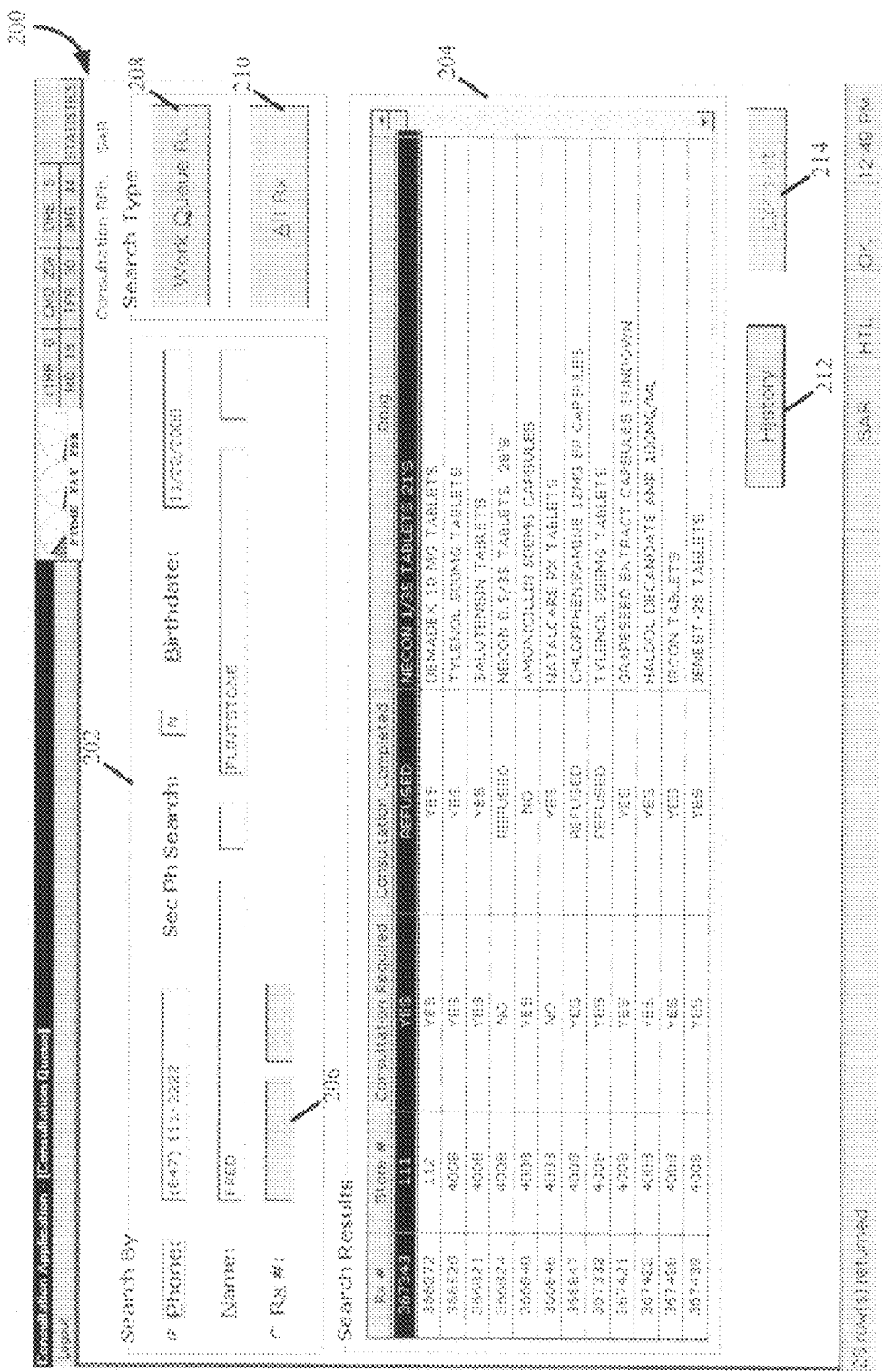
FIG. 6 is an exemplary graphical display that may be provided by a graphical user interface during execution of the consultation application to enable a user to search for a person or medication prescription.

FIG. 6 is an example screen display of a consultation queue view 200 which may be presented to the user upon being granted access to the consultation application 26. The consultation queue view 200 may be used as the main window of the consultation application 26. Generally, the consultation queue view 200 allows a user to enter information about the medication prescription or personal information about the person in order to retrieve the medication prescription data. As shown in FIG. 6, the consultation queue view 200 includes a search view 202 and a results view 204. The search view 202 enables the user to enter search criteria about the medication prescription, such as an alphanumeric identification unique to the medication prescription. The identification information may be entered into a text field 206 using a keyboard or the like, or the user may electrically read the identification information from the physical prescription, such as a prescription printout, a prescription label, prescription packaging, etc.

Identification information on a physical prescription may be provided as a radio frequency identification (RFID) tag, a barcode or any other form of electronic signature unique to the medication prescription. The identification information may be electronically read and entered into the workstation 12. Electronically reading the identification automatically inputs the medication prescription identification to the consultation application 26, which may be demonstrated by populating the text field 206 with a corresponding alphanumeric identification.

Upon receiving the medication prescription identification, the consultation application 26 searches the local data source 14 for medication prescription data of a medication prescription with a corresponding medication prescription identification. In particular, the user may select a graphical representation of a "Work Queue Rx" button 208 which causes the consultation application 26 to search for the medication prescription among data for medication prescriptions that were filled at the pharmaceutical facility and which may be stored within the local data source 14. Alternatively, the search may be defaulted to the local data source 14. As discussed above, data in the local data source 14 may be limited to a specific time period. If the medication prescription does not reside in the local data source 14 or if the medication prescription was previously filled at another location (e.g., another pharmaceutical facility), the user may select an "All Rx" button 210 which causes the consultation application 26 to search for the medication prescription among data for medication prescriptions filled at all pharmaceutical facilities (e.g., all pharmaceutical facilities within a company chain of pharmaceutical facilities and/or within defined geographic boundaries) which may be stored within the central data source 16. A search within the central data source 16 may be limited to a specific time periods, such as the previous year, to avoid results of expired medication prescriptions, and may require the user to provide an identification of the pharmaceutical facility (e.g., a store number). Depending on whether the search is being conducted within the local data source 14 or the central data source 16, the consultation application 26 may enable the corresponding button 208, 210 while disabling the other. Although the consultation application 26 may be arranged to first search the local data source 14 and then the central data source 16, it should be understood that the user may have the option of first searching the central data source 16, or of searching within only one data source.

Upon finding a medication prescription having a matching medication prescription identification, the consultation application 26 may automatically generate a display screen of a consultation review, described further below, which presents information to the user relating to the medication prescription and consultation information. In particular, the consultation review display screen may be automatically generated if a single medication prescription identification is searched and identified within the consultation queue view 200. Additional requirements for automatically generating the consultation review display screen include an indication within the resulting medication prescription data that consultation has not been completed (e.g., "No"), an indication that the medication prescription is active and has an active fill status (e.g., prescription printed or currently being filled) or prescription refill status, and an indication that the medication prescription has no exceptions, beyond those addressed by the consultation, that would otherwise prevent the prescription from being filled.

On the other hand, the consultation application 26 may generate a summary of one or more medication prescriptions matching the medication prescription identification entered by the user in the results view 204, including all medication prescriptions associated with the person or at least all active medication prescriptions associated with the person. Deleted medication prescriptions, such as medications that have expired or been cancelled, may not be displayed even if consultation had been performed.

The results view 204 may display information such as the medication prescription identification, the pharmaceutical facility that previously filled (or is filling) the medication prescription, any associated consultation requirement, results of a previous consultation, and the medication prescription name or summary description. The medication prescription identification may be displayed as the last medication prescription fill number dispensed for the medication prescriptions that meet the search criteria. It is noted that if either a user or a rules engine 28 has indicated that consultation is mandatory for a medication prescription, the indication may be shown in the results view 204. The results of a previous consultation may indicate that consultation was completed (e.g., "Yes"), consultation was not yet completed (e.g., "No") or that consultation was offered but refused (e.g., "Refused"). As such, the user may be offered an opportunity to review the results of the search before proceeding further and/or select the correct medication prescription for the consultation. Although the date/time of previous consultations (or refusal thereof) may be available, the dates/times may not be displayed in order to avoid confusion resulting from different time zones when selecting a medication prescription for consultation, though the dates may be displayed in other display screens.

The consultation application 26 may limit the medication prescriptions displayed in the results view 204 to only those medication prescriptions that have an active fill status, such as prescription printed (e.g., currently being filled) or prescription refill, and that the medication prescription has no exceptions beyond those addressed by the consultation that would otherwise prevent the prescription from being filled. If no medication prescriptions match this criteria, the consultation application 26 may provide the user with a message that consultation is not available for the medication prescription at issue and prompt the user to check the fill status of the medication prescription.

As an alternative to searching for a medication prescription using the medication prescription identification, the user may search for a medication prescription associated with the person by entering one or more search criteria that, individually or in combination, uniquely identify the person, such as name, phone number, birth date, etc. As with searching by medication prescription identification, the user may first search the local data source 14 by selecting the "Work Queue Rx" button 208, and if the medication prescription does not reside in the local data source 14, the user may search the central data source 16 by selecting the "All Rx" button 210. The user may be required to enter two or more search criteria, such as the person's name and phone number, in order to speed up the search time and make the process faster by returning fewer results.

In the event the search criteria entered by the user does not uniquely identify the person, but instead matches the identification of multiple people, the consultation application 26 may generate a patient results window (not shown), which displays a list of all persons having an identification matching the search criteria entered by the user. The user may then select the appropriate person from the list, and the consultation application 26 may generate a display of medication prescriptions associated with that person in the results view 204, from which the user may select the medication prescription for the consultation. The consultation application 26 may limit the user to selecting only one person from the patient results window, which may be indicated by highlighting the selected search result. If the person is not listed within the patient results window and the search was a local search within the local data source 14, the user may return to the consultation queue view 200 to repeat the search within the central data source 16.

Upon finding a medication prescription having a matching identification of the person, the consultation application 26 may automatically generate the display screen of the consultation review as described above, or the consultation application 26 may generate a summary of one or more medication prescriptions matching the identification of the person entered by the user in the results view 204. The results view 204 may display information about the medication prescription as described above, such that the user may be offered an opportunity to review the results of the search before proceeding further and/or select the correct medication prescription for the consultation. For either a medication prescription identification search or a person identification search, the results view 204 may limited the user to selecting only one medication prescription, which may be indicated in the consultation queue view 200 by highlighting the selected medication prescription result.

In selecting a medication prescription from the results view 204, the user may elect to view a consultation history of the medication prescription or view a consultation review display screen to consult the person. The consultation queue view 200 may include a graphical representation of a "History" button 212 which the user may select to view the consultation history of a medication prescription selected from the results view 204. The consultation queue view 200 may also include a graphical representation of a "Consultation" button 214 which the user may select to view consultation information of a medication prescription selected from the results view 204. The user may be prevented from selecting either the "History" button 212 or "Consultation" button 214 until a medication prescription has been selected from the results view 204, after which the buttons 212, 214 may be activated by the consultation application 26.

The graphical representation of the "History" button 212 enables the user to cause the consultation application 26 to generate a display screen or view of a consultation history for a medication prescription selected from the results view 204, for example by selecting the graphical representation of the "History" button 212. It is noted that the graphical representation of the "History" button 212 may be disabled by the consultation application 26 if the results are being limited to only those found in the local data source 14.

Figure 7:
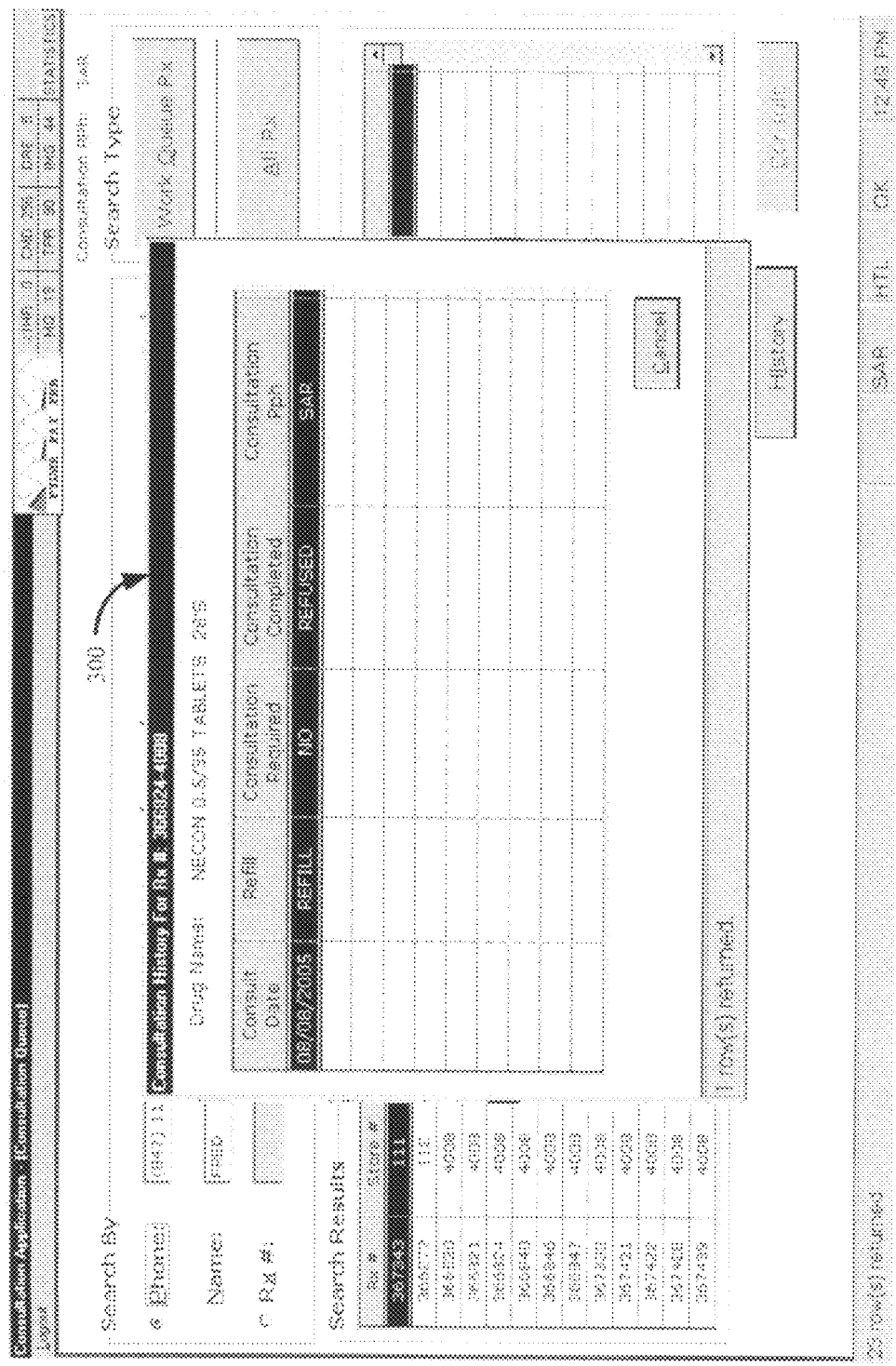
FIG. 7 is an exemplary graphical display that may be provided by a graphical user interface during execution of the consultation application to enable a user to view details regarding a consultation history associated with the medication prescription.

FIG. 7 illustrates an example screen display 300 that may be presented by the consultation application 26 to a user as a consultation history in response to the user selecting a medication prescription from the results view 204 and selecting the graphical representation of the "History" button 212 from the display 200. In particular, the consultation history display 300 may be presented in a separate window, and displays consultation data from the medication prescription data within the local data source 14 or the central data source 16 associated with the medication prescription selected by the user from, the results view 204. For example, each refill of the medication may have required a consultation, or certain criteria or events may have occurred in the history of the medication that caused a consultation. However, the consultation history may be limited to only those medication prescriptions stored in the central data source 16, for example due to time limits imposed on data within the local data source 14.

The consultation application 26 may enable the user to select an entry from the consultation history display 300, which may be indicated by highlighting the selected entry. In response, the consultation application 26 displays an outcome of the consultation and any comments associated with the consultation that may have been provided. The consultation history display 300 may include a summary of each consultation, including, but not limited to, the fill status (e.g., "Refill"), the consultation requirement (e.g., "Yes", "No"), the consultation outcome (e.g., "Accepted", "Refused", blank if consultation not completed), an identification of the consultant of record, and the date/time of the consultation. Each consultation may have associated comments specific to the consultation that may be viewed by selecting the consultation entry (e.g., "double click" with a mouse) and/or selecting a graphical representation of a comments button (not shown). If comments do not exist for the selected consultation, the consultation application 26 may disable any attempt to retrieve comments. It is further noted that the user may be prevented from editing any comments associated with a previous consultation, including adding comments. Consultations for deleted medication prescriptions, such as medications that have expired or been cancelled, may not be displayed even if consultation had been performed.

Referring again to FIG. 6, the graphical representation of the "Consultation" button 214 enables the user to cause the consultation application 26 to generate a display screen or view of a consultation review for a medication prescription selected from the results view 204, for example by selecting the graphical representation of the "Consultation" button 214. The graphical representation of the "Consultation" button 214 may be disabled by the consultation application 26 if the medication prescription data indicates that a consultation has already been performed, for example by showing the consultation results as accepted (e.g., "Yes") or rejected.

Figure 8:
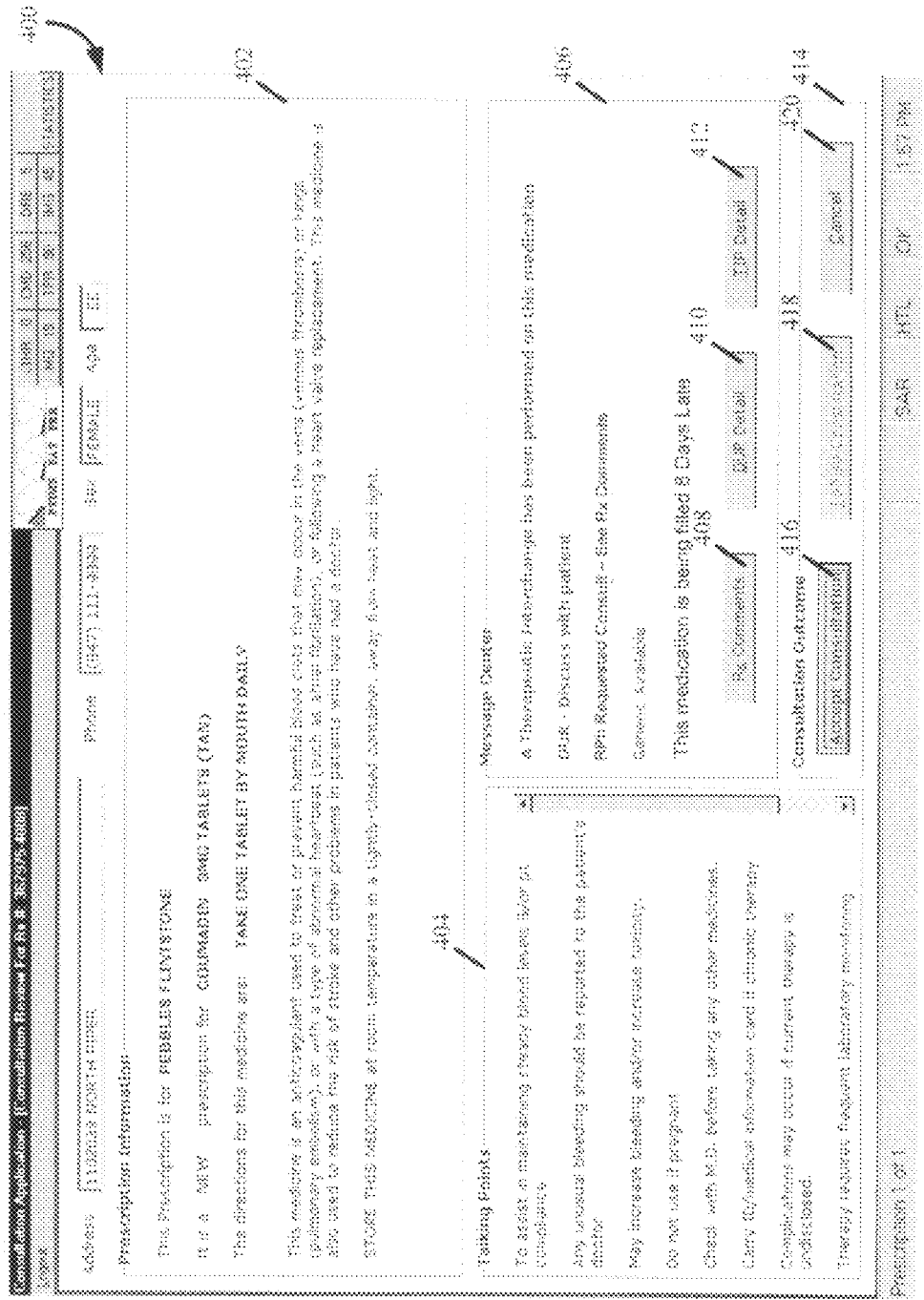
FIG. 8 is an exemplary graphical display that may be provided by a graphical user interface during execution of the consultation application to enable a user to view details regarding the medication prescription and consultation information to be conveyed to the person regarding the medication prescription.

FIG. 8 illustrates an example screen display 400 that may be presented by the consultation application 26 to a user as a consultation review in response to the user selecting a medication prescription from the results view 204 and selecting the graphical representation of the "Consultation" button 214 from the display 200. In particular, the consultation review display 400 may be presented in a separate window, and provides the user with information useful to the user in facilitating a consultation with the person regarding the medication prescription, at least some of which may be conveyed to the person. As shown in FIG. 8, the consultation review display 400 includes a medication prescription view 402 and a discussion view 404, along with a display of the person's identification information, such as address, phone number, gender and age. Generally, the consultation review display 400 provides information associated with a single medication prescription as indicated from the consultation queue view 200. In the event the consultation is a second consultation for a particular medication prescription and to avoid duplicate or conflicting consultations, the consultation application 26 may prevent the user from accessing the consultation review display 400 from the consultation queue view 200, and instead provide the user with access to comments from the previous consultation from the consultation history display 300.

The display of the various views, or the information contained therein, may be dependent on whether the user has accessed the local data source 14 or the central data source 16. For example, some information, such as instructions for storing the medication or talking points, may be developed by a rules engine 28, which may serve several pharmaceutical facilities, including several workstations 12. As such, the results from the rules engine 28, or the rules engine itself 28, may be stored with the central data source 16. If the user has accessed the medication prescription data from the local data source 14, data from the central data source 16 may be unavailable and not displayed in the consultation review display 400.

The medication prescription view 402 provides the user with information about the medication prescription, such as the person associated with the medication prescription, the name of the medication associated with the medication prescription (e.g., Coumadin), the medication dosage and form, (e.g., 3 mg Tablets), the status of the medication prescription (e.g., new, refill, etc.), directions for taking and storing the medication prescription (e.g., "take one tablet by mouth daily"; "store this medication at room temperature in a tightly-closed container, away from heat and light"). The medication prescription view 402 may also include a more detailed description of the medication, including the intended purpose of the medication. The information presented in the medication prescription view 402 may be provided as part of the medication prescription data from the local data source 14 and/or the central data source 16, upon the user's selection of the medication prescription from the consultation queue view 200.

Although any of the information presented in the consultation review display 400 may be conveyed to the person at the user's discretion, the discussion view 404 provides the user with particular items of information that should be conveyed to the person as part of the consultation, and guide the user as to the content of the consultation with the person. In the example provided, the discussion view 404 includes several talking points, including the purpose of the medication, instructions/actions to take based upon observations of the person's reaction to the medication, cautions as to side effects, instructions for use or nonuse, or any other information that may be of importance for the person to know and understand. Although the information presented in the discussion view 404 may be retrieved as part of the medication prescription data, the particulars of the information therein may be the result of comments provided by a pharmaceutical professional, for example from a previous consultation. The information in the discussion view 404 may also be the result of analyses and diagnostics performed by the rules engine 28, which may provide professional counseling information regarding the medication.

As shown in FIG. 8, the consultation review display 400 may also include a message view 406 which provides the user with alerts and messages regarding the medication prescription that may require the further attention of the user, and which may be also used to facilitate the consultation with the person. For example, the message view 406 may includes notifications that the person is late in filling (or refilling) the medication prescription, that the person is on the last refill of the medication prescription and that a generic version of the medication is available to the person. The message view 406 may further include a medication utilization alert (e.g., DUR), a medication interchange alert and/or a requested consultation alert. In order to draw the user's attention to items requiring greater attention by the user, more important items may be highlighted accordingly to draw the user's attention. For example, alerts may be provided in a brighter color, associated with flashing graphics, etc. as compared to messages. Alerts or messages having varying degrees of importance may be identified accordingly. For example, a medication utilization alert may be highlighted in red to signify highest importance, a requested consultation alert may be provided in yellow indicating medium importance and generic availability message may be provided in black indicating lowest importance.

The medication utilization alert may occur if an adverse health outcome has been identified based on the person's utilization of the medication, such as an adverse interaction with another medication, an adverse effect resulting from a health condition of the person, misuse of the medication, etc. The medication utilization alert may be the result of an analysis or diagnostic performed by the rules engine 28, such as a health risk assessment, a compliance assessment, a predictive modeling analysis, identification of inappropriate medications, or an appropriateness analysis of the person's medication regimen. Examples of such analyses and diagnostics are provided in U.S. application Ser. Nos. 11/458,071, 11/458,054, 11/458,080, 11/458,066, and 11/458,075, respectively, which are referenced above. As a result, the user may be notified of any identified adverse health outcome(s) and in turn counsel the person accordingly.

The medication interchange alert may occur if an interchange analysis has been performed on the medication, and resulted in the identification of an alternative replacement medication that has a medical effect that is equivalent to the medication associated with the medication prescription. For example, the replacement medication may have similar beneficial medical effects and the prescribed medication, but with fewer side effects, lower cost, different dosage, etc. The medication interchange alert may also be the result of an analysis or diagnostic performed by the rules engine 28, such as an optimization analysis of the person's medication regimen. Examples of such an analysis or diagnostic is provided in U.S. application Ser. No. 11/458,059, as referenced above. As such, the user may be notified of the replacement medication and counsel the person regarding the same to at least provide the person with the option of utilizing the replacement medication.

The requested consultation alert may occur if a pharmaceutical professional, which may be the user, has requested that a consultation be performed with the person regarding the medication prescription. The reasons for such a request may be numerous, generally at the discretion of the pharmaceutical professional requesting the consultation, and may be provided via comments provided by the requester and stored with the medication prescription data. For example, a consultation may have been required as a result of the medication prescription data review screen 100 which allows a user to review the medication prescription associated with the person, and enables the user to indicate that a consultation is required and to provide comments which may include the reasons for the consultation. As also discussed below, the consultation may have been required as a result of a user indicating a consultation is required when viewing a medication utilization view. Accordingly, a requested consultation alert may alert the user of the consultation application 26 to additional analyses or diagnostics which occur as the result of a pharmaceutical professional's expertise rather than relying solely on automated analyses and diagnostics, such as those provided by the rules engine 28.

As also shown in the message view 406, graphical representations of buttons may be provided corresponding to the different alerts or messages displayed in the message view 406. Each of the graphical representations or buttons enables the user to cause the consultation display 26 to generate a display screen or view of further information associated with an alert or message displayed in the message view 406. For example, a graphical representation of an "Rx Comments" button 408 enables the user to cause the consultation application 26 to generate a comments display screen or view by selecting the graphical representation of the "Rx Comments" button 408. Likewise, a graphical representation of a "Drag Utilization Review (DUR) Detail" button 410 enables the user to cause the consultation application 26 to generate a medication utilization display screen or view by selecting the graphical representation of the "DUR Detail" button 410, and a graphical representation of a "Therapeutic Interchange Program (TIP) Detail" button 412 enables the user to cause the consultation application 26 to generate a medication interchange display screen or view by selecting the graphical representation of the "TIP Detail" button 412. Examples of the comments view, the medication utilization view and the medication interchange view are discussed further below. If an alert or message corresponding with one of the buttons is not displayed in the message view 406, the button may be disabled (e.g., not selectable or displayed) by the consultation application 26.

The consultation review display 400 may also include a consultation outcome view 414 that enables the user to indicate the outcome of the consultation with the person, in addition to providing comments related to the consultation as provided by the comments view discussed below. The consultation outcome view 414 may be provided as graphical representations of buttons that may be selected by the user to indicate various outcomes of the consultation. For example, as shown in FIG. 8, the graphical representations of buttons may include, but are not limited to, an "Accept Consultation" button 416, a "Refuse Consultation" button 418 and a "Cancel" button 420. The "Accept Consultation" button 416 enables the user to indicate that the consultation was accepted by the person as the outcome of the consultation, with corresponding data to be stored with the medication prescription data indicating the consultation was accepted. Similarly, the "Reject Consultation" button 418 enables the user to indicate that the consultation was rejected by the person as the outcome of the consultation, with corresponding data to be stored with the medication prescription data indicating the consultation was rejected. The user may select the "Accept Consultation" button 416 if the person accepts the terms of the consultation, and may select the "Reject Consultation" button 418 if the person does not accept (e.g., does not want or does not have time for) the consultation. The "Cancel" button 420 enables the user to abort the consultation and return to the consultation queue view 200 without providing any indication one way or another as to the outcome of the consultation, or, alternatively, provide an indication that the consultation is incomplete, with corresponding data stored with the medication prescription data. Each of the buttons 416, 418, 420 may be differentiated from one another (e.g., different colors) to avoid selecting the wrong button.

When one of the buttons 416, 418, 420 is selected by the user, the consultation application 26 may record the time/date of the consultation and an identification of the user with the consultation outcome data stored with the medication prescription data. The outcome may then be presented as part of the consultation history shown in FIG. 7 upon subsequent use of the consultation application 26 in relation to the medication prescription and/or the person. However, the consultation application 26 may enable or disable any of the buttons 416, 418, 420, depending on the circumstances of the consultation. For example, if the medication prescription has an exception associated with a medication interchange, the consultation application 26 may disable the "Refuse Consultation" button 418, in order to ensure that consultation is accepted before the person completes a transaction for the medication prescription, and otherwise preventing any such transaction, as discussed above.

After the medication prescription has been consulted upon, the consultation application 26 may cause the consultation review display 400 to be updated with information pertaining to the next medication prescription to be counseled upon (if any) for the person. For example, medication prescriptions that require consultation, but that have not been carried out may appear in the consultation review display 400 one at a time to prompt the user to consult the person, following the medication prescription selected from the consultation queue view 200.

Figure 9:
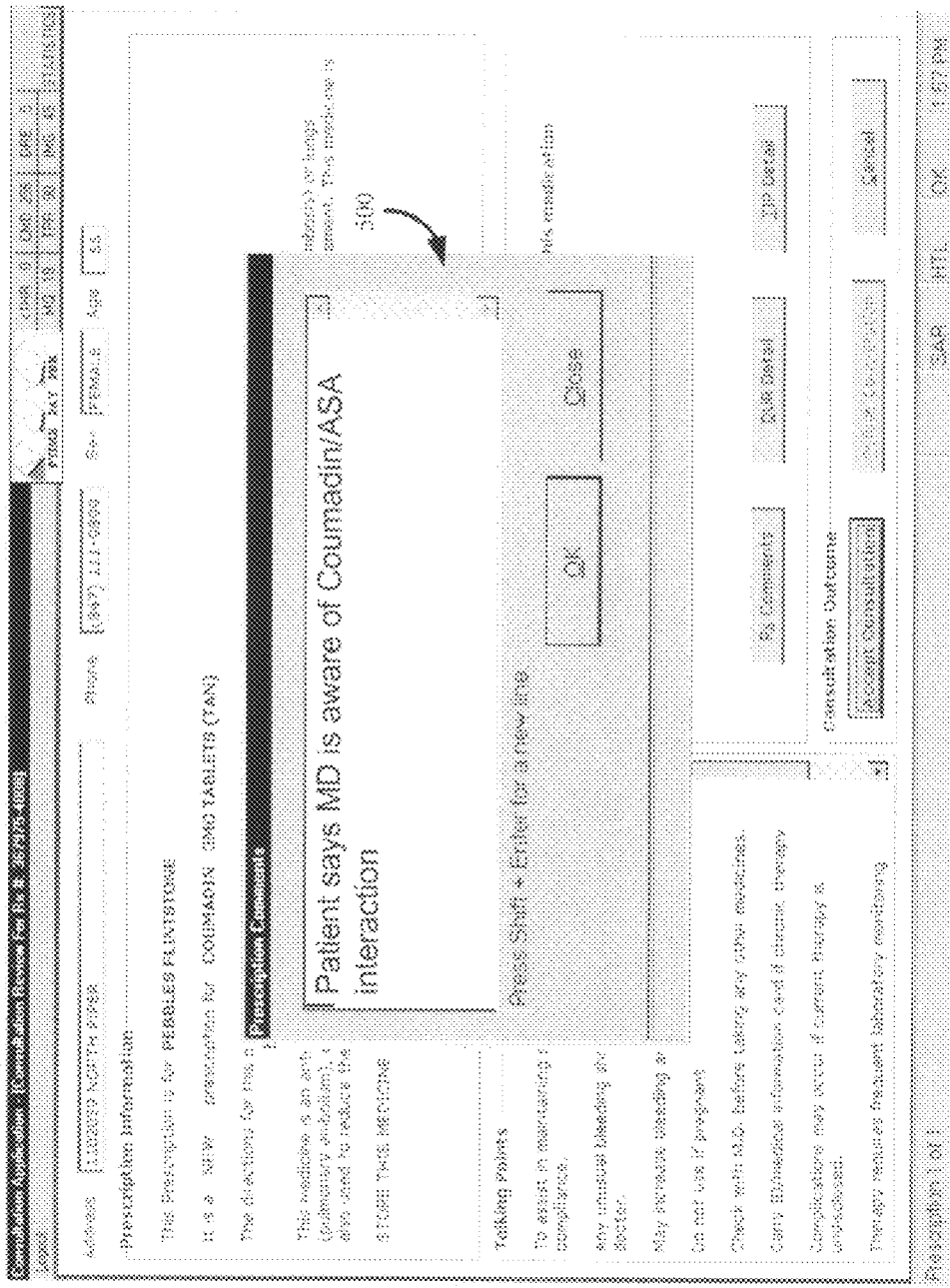
FIG. 9 is an exemplary graphical display that may be provided by a graphical user interface during execution of the consultation application to enable a user to provide comments related to the medication prescription or the consultation.

FIG. 9 illustrates an example screen display 500 that may be presented by the consultation application 26 to a user in response to the user selecting the graphical representation of the "Rx Comments" button 408 from the message view 406. In particular, the comments display 500 may be presented in a separate window, and provides the user with previous comments related to the medication prescription, which may include the reasons for requesting the consultation. The comments display 500 may further allow the user to edit the comments and/or provide additional comments regarding the medication prescription and the consultation for the benefit of other users or for the benefit of the user at a later date. In one example, the consultation application 26 may enable the "Rx Comments" button 408, and hence generate the comments display 500 if comments have been previously provided. Any edits to the comments or additions to the comments may be stored as consultation data, which in turn may be stored with the medication prescription data.

Figure 10:
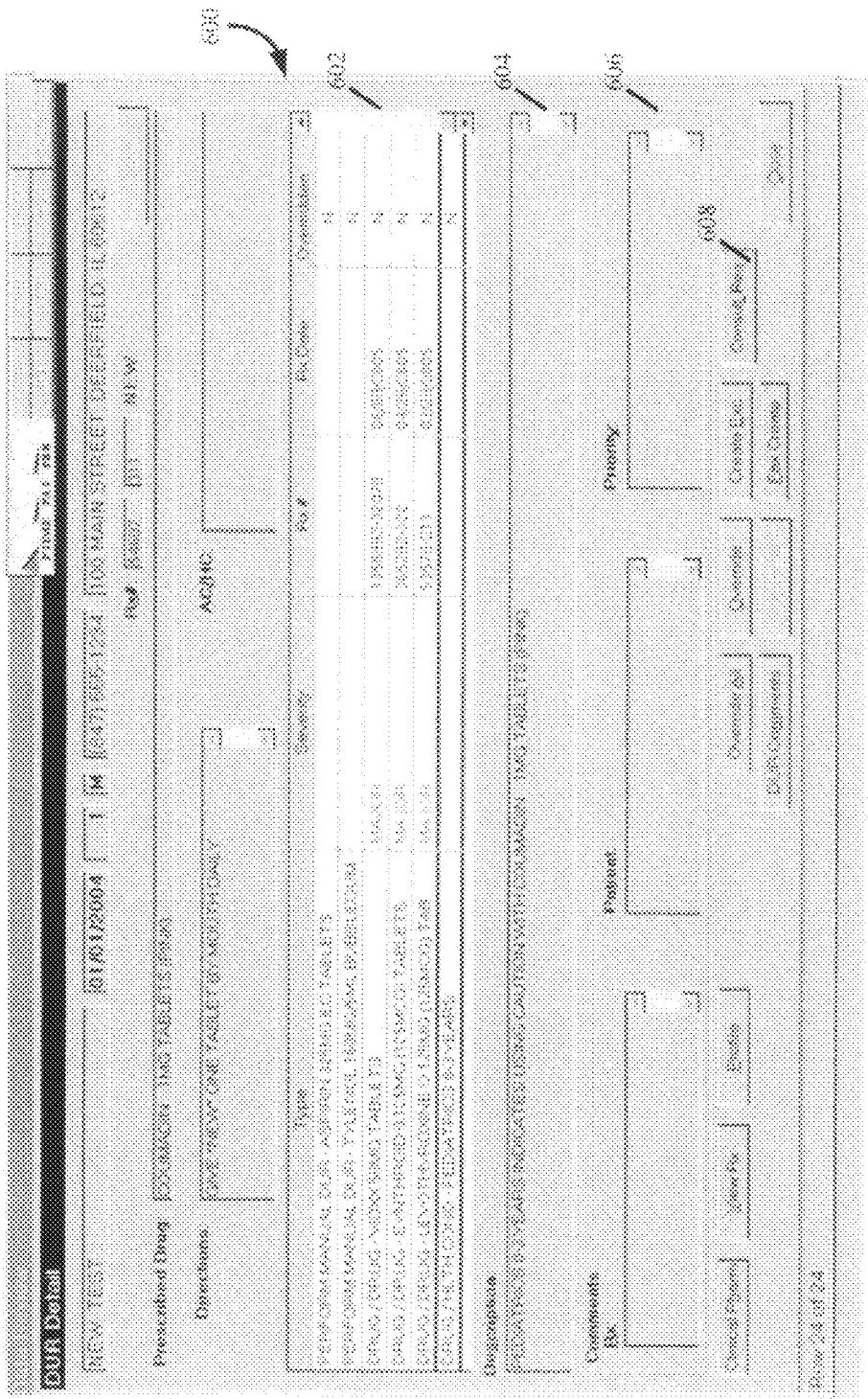
FIG. 10 is an exemplary graphical display that may be provided by a graphical user interface during execution of the consultation application to enable a user to view medication utilization information relating to an identified adverse health outcome associated with the medication.

FIG. 10 illustrates an example screen display 600 that may be presented by the consultation application 26 to a user in response to the user selecting the graphical representation of the "DUR Detail" button 410 from the message view 406. In particular, the medication utilization display 600 may be presented in a separate window, and provides the user with information pertaining to a medication utilization alert. The information within the medication utilization display 600 may include a list 602 of one or more identified adverse health outcomes associated with the medication prescription, including, but not limited to, the type of identified adverse health outcome (e.g., drug-drug interaction, drug-health interaction, etc.), the severity of the identified adverse health outcome (e.g., major), any associated medication prescription identification and date (e.g., Rx #, Rx Date), and whether a user override is permitted. The consultation application 26 may enable the user to select one of the identified adverse health outcomes listed in the medication utilization display 600. In response thereto, the consultation display 26 may generate or populate a description view 604 with a more detailed description of the selected identified adverse health outcome. Alternatively, if the medication utilization alert relates to a particular identified adverse health outcome, for example based upon severity, the consultation display 26 may generate the medication utilization display 600 with the associated identified adverse health outcome already selected and an associated description displayed in the description view 604. As such, the user is presented with information pertinent to the medication utilization alert from the consultation review display 400 and may incorporate the information into the consultation with the person.

A comments view 606 may also be provided to enable the user to enter his/her own comments in relation to the identified adverse health outcome and any associated consultation. In addition, the comments view 606 may also allow for the user to enter any comments provided by the person during the consultation regarding the identified adverse health outcome.

As seen in FIG. 10, the medication utilization display 600 may include a graphical representation of a "Consult Req" button 608. As discussed above, a rules engine 28 may identify one or more adverse health outcomes based upon a person's medication and medical information. Alternatively, a pharmaceutical professional may identify an adverse health outcome based on his/her professional knowledge. In either event, a user viewing the medication utilization display 600 prior to a consultation with the patient may be presented with the identified adverse health outcome(s), in which case the user may select the "Consult Req" button 608 to require consultation with the patient so as to advise the patient as to the identified adverse health outcome(s) associated with the medication prescription before the transaction in completed (and hence before any actual adverse health outcome may occur). During consultation, the user of the consultation application 26 may also select the "Consult Req" button 608 to require a follow-up consultation with the person (for example during a refill of the medication prescription). The follow-up consultation may be used to determine whether the person has been experiencing any symptoms indicative of the onset of the identified adverse health outcome, to provide associated counseling to the person and/or to provide any necessary adjustments to the person's medication regimen. Similar to the "Consult Req" button 114 of FIG. 3, selection of the "Consult Req" button 608 causes the medication prescription data for the medication prescription to be flagged or otherwise associated with an indication that consultation is required, and the person may be prevented from completing a transaction for the medication prescription until consultation has been completed.

Figure 11:
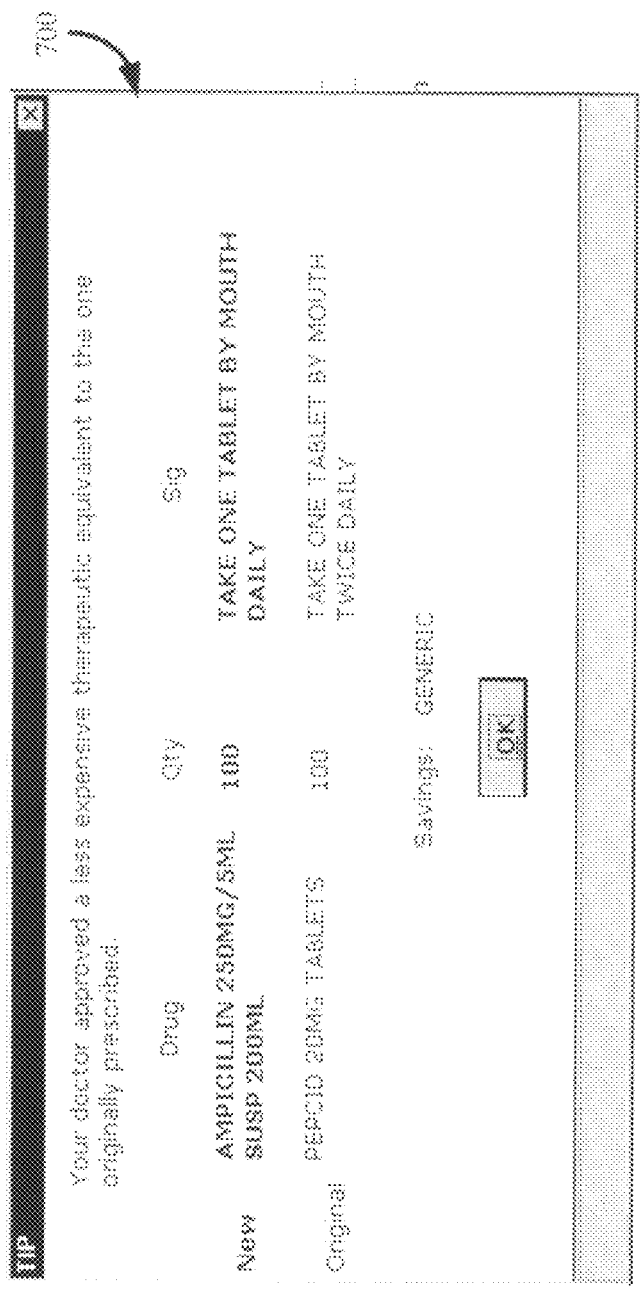
FIG. 11 is an exemplary graphical display that may be provided by a graphical user interface during execution of the consultation application to enable a user to view medication interchange information.

FIG. 11 illustrates an example screen display 700 that may be presented by the consultation application 28 to a user in response to the user selecting the graphical representation of the "TIP Detail" button 412 from the message view 406. In particular, the medication interchange display 700 may be presented in a separate window, and provides the user with information pertaining to a replacement medication that has been identified by the rules engine 26 or a pharmaceutical professional as having a medical effect equivalent to the medication associated with the medication prescription. The reasons for providing a replacement medication are numerous, including, but not limited to, savings in cost, reduced side effects, different dosage, etc. Accordingly, the benefits associated with the replacement medication, including the benefits as compared to the medication of the medication prescription, may be presented in the medication interchange display 700 for the user to convey to the person.

Once consultation has been completed, regardless of the outcome, the medication prescription data is updated with the consultation outcome. Accordingly, when the person attempts to complete the transaction for the medication prescription thereafter, the transaction is permitted or prevented based upon the consultation outcome. For example, if consultation was refused or not completed, as indicated by the user from, the consultation review display 400, and the consultation was mandatory, a pharmaceutical facility personnel may be prompted accordingly and refuse to complete the transaction, or a transaction device may prevent the transaction from being completed.

As discussed above, consultation may be provided between the user and the person at the workstation 12 at a pharmaceutical facility (e.g., in-store). In addition, consultation may also be provided remotely between a workstation 12A and a workstation 12B. For example, a person attempting to complete a transaction at a pharmaceutical location may be prevented from completing the transaction, as discussed above, or may request consultation about their medication prescription, even if consultation is not required. However, if a user qualified to provide the consultation is not available on-site, the consultation application 26 may be conducted remotely, with a user at another geographical location different from that of the person. In one example, the remote consultation is provided remotely via video conferencing and/or instant messaging. As such, consultation may be facilitated even though the person and the user are at different, generally remote, geographic locations in real-time. Although the following example discusses real-time communications facilitated between two workstations 12A, 12B, it should be understood that the person may use any station at the pharmaceutical facility, such as a video display 20A coupled with a communication device 22A that may be used by the person, rather than a workstation 12A as discussed above. On the other hand, it is beneficial for the user to conduct the remote consultation at the workstation 12B in order to utilize the consultation application 26 and facilitate the remote consultation.

In particular, when a person requests or requires consultation, a request for a consultation is sent to the user at the other geographic location. The request may include some minimal information associated with the medication prescription, including an identification of the person and an identification of the medication prescription. In one example, the request is sent via an instant messaging system, which may be implemented in the workstations 12A, 12B, though it should be understood that other methods of notification may be utilized. For example, a request for a consultation received at the workstation 12B may result in an alert displayed on the workstation 12B in order to alert the user to the request. If the user happens to be away from the workstation 12B, the alert may be relayed to the user in addition to, or as an alternative to, displaying the alert on the workstation 12B. Examples of relaying the alert may include a text, voice or video message to a cellular phone, personal digital assistant, pager, or any other communication device that may be proximate to the user.

Once the user has been notified, the medication prescription data for the person is sent to the user's workstation 12B, which may also be sent via instant messaging. In particular, the medication prescription data may be transmitted from the workstation 12A, the local data source 14 and/or the central data source 16, and received at the workstation 12B. Transmission of the medication prescription data to the user's workstation 12B may follow an acceptance of the request for consultation by the user, in order to correlate transmission of the medication prescription data only when the user is present at the workstation 12B. It should further be understood that the communications between the user and the person, and particularly the transmission of medication prescription data, may be secured against unwanted intrusion or interception, for example with the use of secured transmission protocols, encryption, authentication, verification and the like.

At the workstation 12B, the user is presented with the display screens 150-900 of the consultation application 26 as described above, and in particular reviews the consultation review display 400 which displays data useful to the user in facilitating a consultation with the person regarding the medication prescription. Using the consultation application 26, the user may conduct real-time consultation with the person remotely, using the consultation application 26 as described above.

As discussed above, the workstations 12A, 12B may each be equipped with video communication devices 22A, 22B, such as a video camera, microphone and speaker, to facilitate real-time remote video conferencing between the workstations 12A, 12B, and hence real-time remote video conferencing between the user and the person. In particular, a real-time image of the person may be presented to the user at the workstation 12B. The image of the person may be presented in conjunction with one or more of the display screens 150-900. Likewise, a real-time image of the user may be presented to the person at the workstation 12A. In one example, a real-time image of the user may also be presented to the user at the workstation 12B, which may be the same image as presented to the person at the workstation 12A, in order to allow the user to adjust the camera at the workstation 12B to present a well-framed image of the user to the person. In a further example, the user may be provided with control over the communication device 26A at the person's geographic location in order to adjust the person's camera at the workstation 12A to present a well-framed image of the person to the user.

Although the remote consultation utilizes audio and/or video communications, it should be noted that the real-time communications may not be recorded in order to keep the consultation communications confidential and secure. In the event the consultation is requested by the person, but not otherwise required as discussed above, data associated with the consultation (e.g., user comments, results from the consultation, etc.) may also not be recorded or otherwise stored. On the other hand, data associated with mandatory consultations may be recorded and stored in the local data source 14 and/or the central data source 16, as discussed above.

Accordingly, remote consultation between the person and the user may be facilitated even when the user and person are in remote geographic locations. By providing remote consultation, a user is able to consult with a wider field of persons, thereby providing the user with the ability to consult with persons that would otherwise be underserved (e.g., no qualified pharmacist available in the person's locale to provide consultation). Remote consultation may also allow for 24 hour availability, such that even if a local pharmacist is temporarily unavailable for the consultation, a person may remotely consult with another pharmacist or other qualified pharmaceutical professional.

While the consultation application 26 and various methods associated therewith, as described herein, are implemented in software, it may be implemented in hardware, firmware, etc., and may be implemented by any other processor associated with a pharmaceutical facility and other facilities. Thus, the application(s) described herein may be implemented in a standard multi-purpose CPU or on specifically designed hardware or firmware as desired. When implemented in software, the application(s) may be stored in any computer readable memory such as on a magnetic disk, a laser disk, or other storage medium, in a RAM or ROM of a computer or processor, etc. Likewise, the application may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

Although the forgoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A method of pharmaceutical consultation comprising:
    receiving, using a processor, medication prescription data relating to a medication prescription for a person, wherein the medication prescription data comprises an indication regarding a consultation requirement associated with the medication prescription;
    displaying, on a display device, a consultation review screen to the user, wherein the consultation review screen comprises a medication prescription view having information relating to the medication prescription and a discussion view having information to be conveyed to the person regarding the medication prescription as a consultation with the person relating to the medication prescription;
    determining, using a processor-implemented rules engine, if a consultation is mandatory with respect to the medication prescription;
    preventing, using a processor, a transaction related to the medication prescription until consultation indication data is received when the indication regarding the consultation requirement indicates consultation is mandatory, wherein the consultation indication data relates to an indication regarding completion of the consultation with the person relating to the medication prescription; and
    allowing, using a processor, completion of the transaction related to the medication prescription only once the consultation indication data is received.

2. The method of claim 1, further comprising:
    displaying, on a display device, a medication prescription review screen to a user comprising information relating to the medication prescription;
    enabling, using a processor, the user to request a consultation requirement for the medication prescription; and
    setting, using a processor, the indication regarding the consultation requirement associated with the medication prescription as a mandatory consultation in response to the request for the consultation requirement for the medication prescription.

3. The method of claim 2, wherein the medication prescription review screen comprises a patient information view having information relating to the person, a medication information view having information relating to the medication prescription and a prescriber information view having information relating to a person prescribing the medication prescription, the method further comprising:
    enabling, using a processor, the user to approve information in each of the patient information view, the medication information view and the prescriber information view; and
    disabling, using a processor, enablement of the user to request a consultation requirement for the medication prescription until the information in each of the patient information view, the medication information view and the prescriber information view has been approved.

4. The method of claim 2, wherein the consultation review screen comprises the indication regarding the consultation requirement associated with the medication prescription as a mandatory consultation.

5. The method of claim 1, further comprising prompting, using a processor, a user with the indication regarding the consultation requirement associated with the medication prescription.

6. The method of claim 5, wherein the indication regarding the consultation requirement indicates consultation is one of the group consisting of: an optional consultation, a medication interchange consultation relating to a replacement medication having a medical effect equivalent to a medication associated with the medication prescription for the person, a medication utilization consultation relating to an identified adverse health outcome associated with utilization of the medication and a requested consultation.

7. The method of claim 6, further comprising:
receiving, using a processor, data relating to the person's acceptance or rejection of the optional consultation if the user is prompted with the optional consultation indication; and
permitting, using a processor, a transaction related to the medication prescription if the indication regarding the consultation requirement comprises the optional.

8. The method of claim 1, further comprising displaying, on a display device, a consultation queue screen to the user, wherein the consultation queue screen comprises one or more entries for search criteria to enable the user to conduct a search for data relating to the medication prescription.

9. The method of claim 8, wherein the one or more entries for search criteria comprises one or more entries for an identification of the medication prescription, the method further comprising:
receiving, using a processor, identification data relating to the identification of the medication prescription; and
wherein displaying the consultation review screen comprises automatically displaying, on a display device, the consultation review screen comprising consultation information relating to a medication prescription having attributes matching the identification of the medication prescription.

10. The method of claim 8, wherein the one or more entries for search criteria comprises one or more entries for an identification of the person, the method further comprising:
receiving, using a processor, information relating to search criteria comprising an identification of the person; and
wherein displaying a consultation queue screen comprises displaying, on a display device, a consultation queue screen having information relating to one or more medication prescriptions of a person having attributes matching the search criteria.

11. The method of claim 10, wherein the consultation queue screen further comprises an indication regarding a consultation requirement associated with each of the one or more medication prescriptions of the person having attributes matching the search criteria.

12. The method of claim 10, wherein the consultation queue screen further comprises information relating to a status of a consultation for each of the one or more medication prescriptions of the person having attributes matching the search criteria.

13. The method of claim 10, further comprising:
enabling, using a processor, the user to select a medication prescription displayed on the consultation queue screen;
enabling, using a processor, the user to request the consultation history of the selected medication prescription; and
displaying, on a display device, a consultation history screen in response to the request for the consultation history, wherein the consultation history screen comprises information relating to a consultation history between a pharmacist and the person for the selected medication prescription.

14. The method of claim 10, further comprising:
enabling, using a processor, the user to select a medication prescription displayed on the consultation queue screen;
enabling, using a processor, the user to request a consultation review of the selected medication prescription; and
displaying, on a display device, the consultation review screen in response to the request for the consultation review.

15. The method of claim 1, further comprising:
enabling, using a processor, the user to provide data indicating acceptance of the consultation by the person;
enabling, using a processor, the user to provide data indicating rejection of the consultation by the person; and
permitting, using a processor, a transaction relating to the medication prescription in response to receiving data indicating acceptance of the consultation by the person,
wherein preventing a transaction relating to the medication prescription comprises preventing, using a processor, a transaction relating to the medication prescription in response to receiving data indicating rejection of the consultation by the person.

16. The method of claim 1, further comprising:
enabling, using a processor, the user to provide consultation data relating to the consultation between the user and the person regarding the medication prescription; and
storing, in a memory, the consultation data as consultation information relating to the medication prescription.

17. The method of claim 1, wherein the consultation review screen further comprises a message view having information relating to alerts regarding the medication prescription.

18. The method of claim 17, further comprising:
enabling, using a processor, the user to request medication utilization information regarding the medication prescription in response to a medication utilization alert regarding the medication prescription;
displaying, on a display device, a medication utilization view in response to the request for the medication utilization information, the medication utilization review having a list of one or more identified adverse health outcomes associated with utilization of a medication associated with the medication prescription.

19. The method of claim 17, the method further comprising:
enabling, using a processor, the user to request medication interchange information regarding the medication prescription in response to a medication interchange alert regarding the medication prescription;
displaying, on a display device, a medication interchange view in response to the request for the medication interchange information, the medication interchange view having information relating to a replacement medication having a medical effect equivalent to a medication associated with the medication prescription.

20. The method of claim 1, wherein the consultation review screen further comprises consultation information relating to consultation instructions for the user.

21. A pharmaceutical consultation system for use in a pharmaceutical facility comprising:
a database adapted to store medication prescription data comprising one or more medication prescription data entries each relating to a medication prescription for a person and each comprising medication prescription consultation data related to information to be conveyed to a person in a consultation regarding the related medication prescription, and each comprising an indication regarding a consultation requirement associated with the medication prescription;
a display application stored on a computer readable memory and adapted to be executed on a processor to create a consultation display for the medication prescription data stored in the database, the consultation display including a consultation view and an outcome view having one or more graphical representations each relating to an outcome of the consultation, wherein the display application enables a user to select one of the one or more medication prescription data entries to specify medication prescription consultation data to be displayed and presents the medication prescription consultation data in the consultation view, and enables the user to select one of the one or more graphical representations relating to an outcome of the consultation to be stored within the database in the selected medication prescription data entry;
a processor-implemented rules engine adapted to determine if a consultation is mandatory with respect to the medication prescription; and
a processor adapted to prevent a transaction related to the medication prescription until consultation indication data is received when the indication regarding the consultation requirement indicates consultation is mandatory, wherein the consultation indication data relates to an indication regarding completion of the consultation with the person relating to the medication prescription, and further adapted to allow completion of the transaction related to the medication prescription only once the consultation indication data is received.

22. The pharmaceutical consultation system of claim 21, wherein the medication prescription consultation data further relates to one or more messages regarding the related medication prescription, wherein the consultation display further includes a message view, and wherein the display application enables the user to select one of the one or more medication prescription data entries to specify medication prescription consultation data to be displayed and presents the one or more messages regarding the related medication prescription in the message view.

23. The pharmaceutical consultation system of claim 22, wherein the display application is adapted to be executed on a processor to create a medication utilization display, wherein at least one of the one or more messages comprises a medication utilization alert and the message view further includes a graphical representation relating to the medication utilization alert, and wherein the display application enables a user to select the graphical representation relating to the medication utilization alert to display the medication utilization display and presents medication utilization data related to one or more identified adverse health outcome associated with utilization of a medication associated with the selected medication prescription data entry.

24. The pharmaceutical consultation system of claim 22, wherein the display application is adapted to be executed on a processor to create a medication interchange display, wherein at least one of the one or more messages comprises a medication interchange alert and the message view further includes a graphical representation relating to the medication interchange alert, and wherein the display application enables a user to select the graphical representation relating to the medication interchange alert to display the medication interchange display and presents medication interchange data related to a replacement medication having a medication effect equivalent to a medication associated with the selected medication prescription data entry.

25. The pharmaceutical consultation system of claim 21, wherein the consultation display further comprises a medication prescription view having medication prescription data related to the selected medication prescription data entry.

26. The pharmaceutical consultation system of claim 21, wherein the display application is adapted to be executed on a processor to create a consultation queue display, the consultation queue display including a search view having one or more data entries to input search criteria and a results view, wherein the display application enables the user to provide search criteria via the one or more data entries in the search view.

27. The pharmaceutical consultation system of claim 26, wherein the search criteria comprises an identification of a medication prescription and wherein the display application automatically generates the consultation display for medication prescription data stored in the database that comprises attributes corresponding to the identification of the medication prescription.

28. The pharmaceutical consultation system of claim 26, wherein the search criteria comprises an identification of a person and wherein the display application presents one or more of the medication prescription data entries of a person having attributes matching the search criteria in the results view and enables the user to select different ones of the one or more medication prescription data entries presented in the results view.

29. The pharmaceutical consultation system of claim 28, wherein the display application enables the user to select different ones of the one or more medication prescription data entries presented in the results view to specify medication prescription consultation data relating to the selected medication prescription data entry to be displayed and presents medication prescription consultation data associated with a selected medication prescription data entry in the consultation view.

30. The pharmaceutical consultation system of claim 28, wherein the display application is adapted to be executed on a processor to create a medication history display and enables the user to select different ones of the one or more medication prescription data entries presented in the results view to specify medication prescription history data relating to the selected medication prescription data entry to be displayed and presents medication prescription history data associated with the selected medication prescription data entry in the medication prescription history view.

31. The pharmaceutical consultation system of claim 21, wherein one or more of the displays includes a medication utilization view having a list of one or more identified adverse health outcomes associated with utilization of the medication, wherein the display application enables a user to be alerted within the consultation view to an identified adverse health outcome associated with utilization of the medication and presents the one or more identified adverse health risk outcomes associated with utilization of the medication within the medication utilization view.

32. The pharmaceutical consultation system of claim 31, wherein the display application enables a user to view data relating to details of a selected one of the one or more adverse health risks.

33. The pharmaceutical consultation system of claim 21, wherein one or more of the displays includes a medication interchange view having data relating to a replacement medication having a medical effect equivalent to a medication associated with the medication prescription for the person, wherein the display application enables a user to be alerted within the consultation view to a medication interchange opportunity and presents replacement medication data relating to the replacement medication and medication prescription data relating to the selected medication prescription entry to be displayed within the therapeutic interchange view as a comparison of attributes between the replacement medication and the prescription medication.

34. The pharmaceutical consultation system of claim 33, wherein the display application enables a user to view an advantageous attribute of the replacement medication as compared to the prescription medication.

\* \* \* \* \*

UNITED STATES PATENT AND TRADEMARK OFFICE
CERTIFICATE OF CORRECTION

| | | |
|---|---|---|
| PATENT NO. | : 8,676,604 B2 | Page 1 of 1 |
| APPLICATION NO. | : 11/839306 | |
| DATED | : March 18, 2014 | |
| INVENTOR(S) | : Kozlowski et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1726 days.

Signed and Sealed this
Second Day of June, 2015

Michelle K. Lee
*Director of the United States Patent and Trademark Office*